(12) United States Patent
Kim et al.

(10) Patent No.: US 7,718,681 B2
(45) Date of Patent: May 18, 2010

(54) 5-(1,3-DIARYL-1H-PYRAZOL-4-YLMETHYLENE)-THIAZOLIDINE,2,4-DIONE DERIVATIVES USEFUL AS ANTICANCER AGENT

(75) Inventors: Hyoung Rae Kim, Daejeon (KR); Jaesung No, Chungcheongnam-do (KR); Min Jung Seo, Daejeon (KR); Bo Gan Song, Daejeon (KR); Bum Suk Son, Busan (KR); Jung Ki Kim, Daejeon (KR); Kwang-Rok Kim, Daejeon (KR); Hyae Gyeong Cheon, Daejeon (KR); Ge Hyeong Lee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 428 days.

(21) Appl. No.: 11/884,583

(22) PCT Filed: Feb. 3, 2006

(86) PCT No.: PCT/KR2006/000401

§ 371 (c)(1),
(2), (4) Date: Aug. 16, 2007

(87) PCT Pub. No.: WO2006/101307

PCT Pub. Date: Sep. 28, 2006

(65) Prior Publication Data

US 2008/0275094 A1    Nov. 6, 2008

(30) Foreign Application Priority Data

Mar. 24, 2005    (KR) ..................... 10-2005-0024688

(51) Int. Cl.
*A61K 31/427*    (2006.01)
*C07D 417/06*    (2006.01)
(52) U.S. Cl. ..................... 514/369; 548/183
(58) Field of Classification Search ..................... None
See application file for complete search history.

(56) References Cited

FOREIGN PATENT DOCUMENTS

| WO | WO 96/11196 | 4/1996 |
|----|-------------|--------|
| WO | WO 03/032598 | 4/2003 |

*Primary Examiner*—Kamal A Saeed
(74) *Attorney, Agent, or Firm*—Frommer Lawrence & Haug LLP; Ronald R. Santucci

(57) ABSTRACT

The present invention relates to a 5-(1,3-diaryl-1H-pyrazol-4-ylmethylene)-thiazolidine-2,4-dione derivative or its pharmaceutically acceptable salts thereof, a method for preparing the same and an anticancer agent composition comprising the same as an active ingredient.

4 Claims, 1 Drawing Sheet

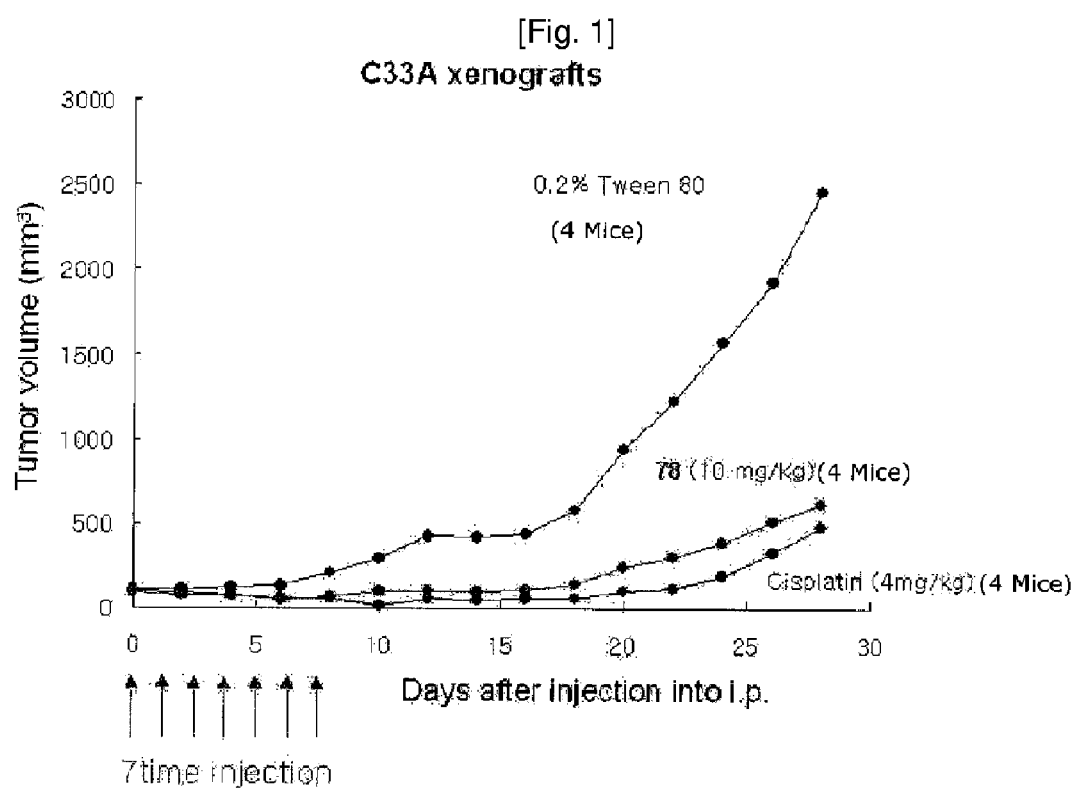

5-(1,3-DIARYL-1H-PYRAZOL-4-YLMETHYLENE)-THIAZOLIDINE,2,4-DIONE DERIVATIVES USEFUL AS ANTICANCER AGENT

This application is a 371 of PCT/KR2006/000401 filed on Feb. 3, 2006, published on Sep. 28, 2006 under publication number WO 2006/101307 A1 which claims priority benefits from Korean Patent Application No. 10-2005-0024688 filed Mar. 24, 2005, the disclosure of which is hereby incorporated by reference.

TECHNICAL FIELD

The present invention relates to a 5-(1,3-diaryl-1H-pyrazol-4-ylmethylene)-thiazolidine-2,4-dione derivative or its pharmaceutically acceptable salts thereof, a method for preparing the same and a composition for an anticancer agent comprising the same as an active ingredient.

BACKGROUND ART

CDC25B is a phosphatase playing an important role in determining G2/M phase transition during cell division. Inhibition of CDC25B activity hinders cell division, and consequently, results in cell death; that is, it is related with anticancer action. Hyperexpression of CDC25B was observed in most tumors including stomach cancer (*Jpn. J. Cancer Res.* 1997, 88, 9947), colon cancer (*Exp. Cell Res.* 1998, 240, 236; *Lab. Invest.* 2001, 81, 465), lung cancer (*Cancer Res.* 1998, 58, 4082), brain cancer and laryngeal cancer (*Cancer Res.* 1997, 57, 2366), breast cancer (*Cancer Statistics in Japan* 1997 Foundation for Promotion of Cancer Research, Tokyo, Jpn.), etc. Abnormal proliferations of mammary glands were observed in a transgenic mouse in which CDC25B was overexpressed (*Oncogene* 1999, 18, 4561). It was also reported that breast cancer is easily induced when treated with a carcinogen (9,10-dimethyl-1,2-benzanthracene) to the transgenic mouse. Accordingly, CDC25B is an important target in developing an anticancer agent. That is, development of an anticancer agent capable of inhibiting CDC25B with little cytotoxicity to normal cells will be desirable.

EP 379979 A1 discloses that a 5-(substituted-1H-pyrazol-4-ylmethylene)-thiazolidine-2,4-dione derivative, with the pyrazole group at the 5-position of the thiazole having a pyrazolopyridine structure, can be used as adenosine antagonist.

Japanese Patent No. 55029804 discloses that the silver halide of a 5-(substituted-1H-pyrazol-4-ylmethylene)-thiazolidine-2,4-dione derivative, with the pyrazole group at the 5-position of the thiazole having a pyrazolone structure, is useful as a dye that inhibits blurring and photoemission in a photosensitizer.

DISCLOSURE

The present inventors completed the present invention by discovering that the 5-(1,3-diaryl-1H-pyrazol-4-ylmethylene)-thiazolidine-2,4-dione derivative has a selective inhibitory activity against CDC25B, a selectivity for similar other phosphatases and possesses an anticancer activity.

Therefore, in an embodiment of the present invention, there is provided a 5-(1,3-diaryl-1H-pyrazol-4-ylmethylene)-thiazolidine-2,4-dione derivative or its pharmaceutically acceptable salts.

In an embodiment of the present invention, there is provided a method for preparing the 5-(1,3-diaryl-1H-pyrazol-4-ylmethylene)-thiazolidine-2,4-dione derivative or the pharmaceutically acceptable salt thereof.

In a further embodiment of the present invention, there is provided a composition for an anticancer agent comprising the 5-(1,3-diaryl-1H-pyrazol-4-ylmethylene)-thiazolidine-2,4-dione derivative or its pharmaceutically acceptable salts.

DESCRIPTION OF DRAWINGS

FIG. 1 shows the result of in vivo anticancer effect of several candidate inhibitors against CDC25B tested using a human tumor model.

BEST MODE

The present invention provides a 5-(1,3-diaryl-1H-pyrazol-4-ylmethylene)-thiazolidine-2,4-dione derivative represented by the following formula 1 or a pharmaceutically acceptable salt thereof:

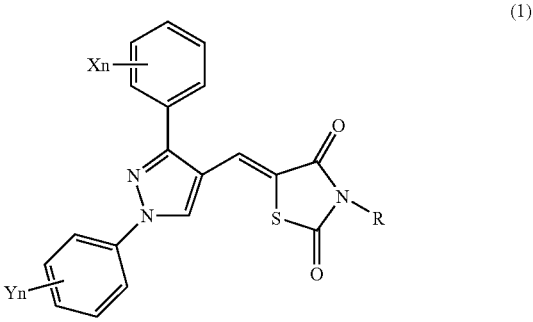

(1)

wherein

X is hydrogen, $C_1$-$C_4$alkyl, $C_1$-$C_4$haloalkyl, a halogen atom, $C_1$-$C_4$alkoxy unsubstituted or substituted with $C_1$-$C_4$alkylcarboxyl, $C_1$-$C_4$haloalkoxy, $C_3$-$C_4$alkenyloxy, $C_2$-$C_4$acyl, $C_3$-$C_{10}$cycloalkylalkoxy, $C_3$-$C_{10}$cycloalkyloxy, hydroxy, cyano or nitro;

Y is hydrogen, $C_1$-$C_4$alkyl, a halogen atom, $C_1$-$C_4$alkoxy, $C_3$-$C_4$alkenyloxy, $C_2$-$C_4$acyl, cyano or nitro;

n is an integer of from 1 to 5; and

R is hydrogen, $C_1$-$C_4$alkyl, $C_2$-$C_4$alkenyl, $C_3$-$C_4$alkynyl, $C_1$-$C_4$haloalkyl, $C_2$-$C_4$alkoxyalkyl or benzyl.

In a preferred embodiment of the present invention, in the formula 1,

X is $C_1$-$C_4$alkyl, $C_1$-$C_4$haloalkyl, a halogen atom, $C_1$-$C_4$alkoxy unsubstituted or substituted with $C_1$-$C_4$alkylcarboxyl, $C_1$-$C_4$haloalkoxy, $C_3$-$C_{10}$cycloalkylalkoxy, $C_3$-$C_{10}$cycloalkyloxy, hydroxy, $C_3$-$C_4$alkenyloxy or nitro;

Y is hydrogen, $C_1$-$C_4$alkyl, a halogen atom, $C_1$-$C_4$alkoxy, $C_3$-$C_4$alkenyloxy, $C_2$-$C_4$acyl, cyano or nitro;

n is an integer of from 1 to 3; and

R is hydrogen, $C_1$-$C_4$alkyl, $C_1$-$C_4$haloalkyl, $C_2$-$C_4$alkoxyalkyl or benzyl.

In another preferred embodiment of the present invention, in the formula 1,

X is isopropyl, trifluoromethyl, t-butyl, bromine, chlorine, iodine, ethyl, methoxy, ethoxy, propyloxy, benzyloxy, allyloxy, cyclopropylmethoxy, cyclopentyloxy, hydroxy, fluoromethoxy, ethylcarboxyl-substituted methoxy or nitro;

Y is hydrogen, methyl, ethyl, fluorine, chlorine, bromine, iodine, methoxy, ethoxy, cyano or nitro;

n is an integer of from 1 to 3; and

R is hydrogen, methyl, ethyl, propano, propyl, propenyl, propynyl, $C_1$-$C_4$fluoroalkyl, benzyl or benzyloxy.

In a further preferred embodiment of the present invention, in the formula 1,

X is methoxy or nitro in which the 2-position is substituted with bromine, chlorine, methoxy or nitro, 4-position is substituted with trifluoromethyl, methoxy, ethoxy, propyloxy, propynyloxy, fluoromethoxy, iodine, benzyloxy or allyloxy and the 3-position and the 5-position are substituted with isopropyl, t-butyl, bromine, iodine, methoxy, ethoxy, propyloxy, cyclopropylmethoxy, cyclopentyloxyhydroxyl or ethylcarboxyl;

Y is hydrogen, methyl or ethyl;

n is an integer of from 1 to 3; and

R is hydrogen, methyl, ethyl, propyl, propenyl, propynyl, benzyloxy, sodium, benzyl or methoxy substituted with ethylcarboxyl.

In the formula 1, X may be present at the 1- to 5-position s of the phenyl group, preferably at the 2-, 3-, 4- or 5-position. Y may be present at the 1- to 5-position s, preferably at the 1-, 2- or 3-position.

In the most preferred embodiment of the present invention, the compound represented by the formula 1 is 5-[3-(2-chlorophenyl)-1-phenyl-1H-pyrazol-4-ylmethylene]-thiazolidine-2,4-dione, 5-[3-(3-nitro)-1-phenyl-1H-pyrazol-4-ylmethylene]-3-methyl-thiazolidine-2,4-dione, 5-[3-(3-trifluoromethyl)-1-phenyl-1H-pyrazol-4-ylmethylene]-thiazolidine-2,4-dione, 5-[3-(3-chloro-4-ethoxy-phenyl)-1-phenyl-1H-pyrazol-4-ylmethylene]-3-methyl-thiazolidine-2,4-dione, 5-[3-(3-chloro-4-propyloxy-phenyl)-1-phenyl-1H-pyrazol-4-ylmethylene]-thiazolidine-2,4-dione, 5-[3-(3-bromo-4-ethoxy-phenyl)-1-phenyl-1H-pyrazol-4-ylmethylene]-3-methyl-thiazolidine-2,4-dione, 5-[3-(3-bromo-4-propyloxy-phenyl)-1-phenyl-1H-pyrazol-4-ylmethylene]-3-methyl-thiazolidine-2,4-dione or a pharmaceutically acceptable salt thereof.

Unless specified otherwise, the term 'alkyl' used herein refers to a linear or branched, saturated hydrocarbon radical having 1 to 4 carbon atoms.

Unless specified otherwise, the term 'halogen' or 'halo' used herein refers to a halogen atom and includes fluorine, chlorine, bromine, iodine and fluorine.

Unless specified otherwise, the term 'alkoxy' used herein refers to O-alkyl ('alkyl' is the same as defined above).

Unless specified otherwise, the term 'alkenyl' used herein refers to an unsaturated hydrocarbon radical having a double bond and having 2 to 4 carbon atoms.

Unless specified otherwise, the term 'alkynyl' used herein refers to an unsaturated hydrocarbon radical having a triple bond and having 3 or 4 carbon atoms.

Unless specified otherwise, the term 'acyl' used herein refers to an 'aroyl' group derived from an aliphatic carboxylic acid, such as acetyl, propionyl, etc.

Unless specified otherwise, the term 'cycloalkylalkoxy' used herein refers to a radical having 3 to 10 carbon atoms, in which alkoxy is bonded with a saturated hydrocarbon ring.

Unless specified otherwise, the term 'cycloalkyloxy' used herein refers to a radical having 3 to 10 carbon atoms, in which oxygen is bonded with a saturated hydrocarbon ring.

Unless specified otherwise, the term 'alkenyloxy' used herein refers to a radical having 3 or 4 carbon atoms, in which oxygen is bonded with an unsaturated hydrocarbon having a double bond.

Unless specified otherwise, the term 'haloalkyl' used herein refers to an alkyl (defined above) radical, in which a hydrogen atom is substituted with a halogen atom.

Unless specified otherwise, the term 'haloalkoxy' used herein refers to an alkoxy (defined above) radical, in which a hydrogen atom is substituted with a halogen atom.

The present invention also provides pharmaceutically acceptable salts of the compound represented by the formula 1. The above salts may be prepared by the methods known in the related art. The above pharmaceutically acceptable salts may be any pharmaceutically acceptable salt, for example, a salt of organic or inorganic acid, such as hydrochloride, hydrobromide, sulfate, phosphate, acetate, citrate, fumarate, lactate, maleate, succinate and tartarate, an alkali metal salt, such as sodium salt and potassium salt, or an ammonium salt.

The present invention also provides a method of preparing the compound represented by the formula 1 or its pharmaceutically acceptable salts comprising: reacting the compound represented by the formula 2 below with the compound represented by the formula 3 below to obtain the compound represented by the formula 4 below; obtaining the compound represented by the formula 5 below from Vilsmeier-Haack reaction of the compound represented by the formula 4; and reacting the compound represented by the formula 5 with thiazolo-2,4-dione to obtain the compound represented by the formula 1, in which R is H, or reacting the product with the compound represented by the formula 6 below to obtain the compound represented by the formula 1, in which R is as follows:

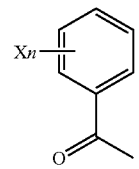

(2)

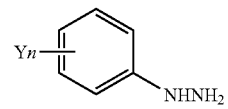

(3)

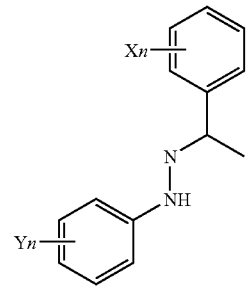

(4)

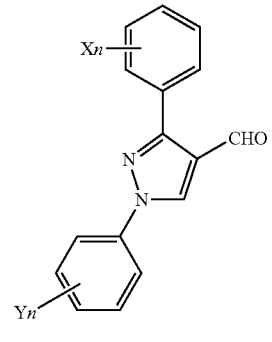

(5)

R—Z (6)

wherein

X, Y, n and R are the same as defined above; and

Z, a leaving group, is a halogen atom, such as chlorine, bromine and iodine, toluenesulfonyloxy or methanesulfonyloxy.

The preparation method of the present invention may be expressed by the following scheme 1.

[Scheme 1]

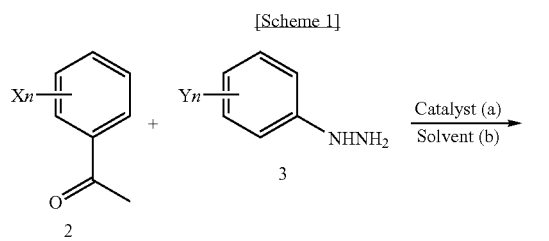

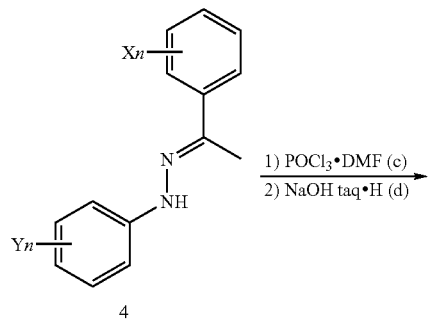

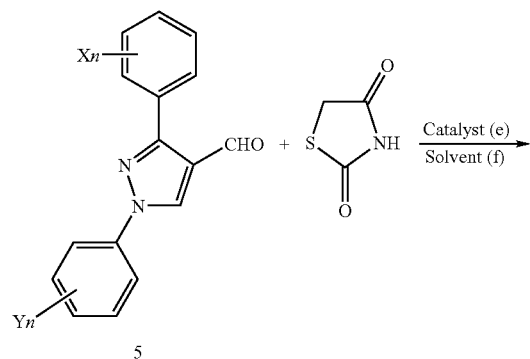

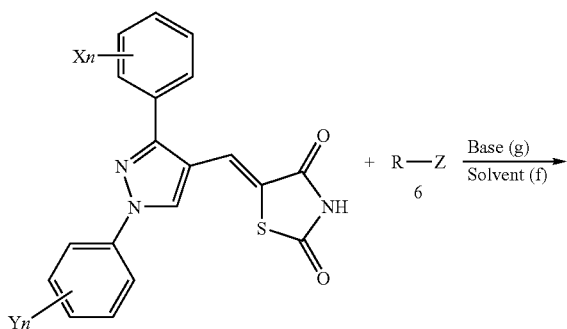

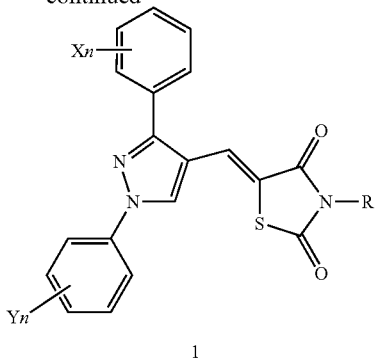

a: acetic acid or benzoic acid b: alcohol such as methanol and ethanol, water or organic solvent c: anhydrous dimethylformamide (DMF)/phosphorus oxychloride (POCl$_3$), thionyl chloride or oxalyl chloride d: sodium hydroxide solution e: a salt of weak acid, such as acetic acid and benzoic acid, or weak base, such as pyridine, amine and aniline f: an organic solvent such as benzene and toluene g: inorganic base, such as potassium carbonate, sodium carbonate, sodium hydroxide, calcium hydroxide and cesium carbonate, or organic base, such as triethylamine and pyridine h: dimethylformamide (DMF), tetrahydrofuran (THF), acetone, water or other organic solvent First, the substituted acetophenone of the formula 2 is reacted with the substituted hydrazine of the formula 3 to obtain the hydrazone derivative of the formula 4. An alcohol such as methanol or ethanol, water or other organic solvent may be used as a solvent in this reaction. Preferably, an alcohol such as methanol or ethanol is used. As the catalyst, a small amount of a weak acid such as acetic acid or benzoic acid may be used.

Then, the hydrazone derivative of the formula 4 is transformed to the 3-aryl-pyridyl-pyrazol-4-carboxaldehyde derivative of the formula 5 using anhydrous dimethylformamide (DMF) as a solvent and phosphorus oxychloride (POCl$_3$), thionyl chloride or oxalyl chloride, preferably phosphorus oxychloride as catalyst.

Next, the pyrazolecarboxaldehyde of the formula 5 is reacted with thiazolidine-2,4-dione to obtain the compound of the formula 1, in which R is H. Benzene, toluene or other organic solvent may be used in this reaction. Preferably, benzene or toluene is used as a solvent. For the catalyst, a mixture of acetic acid and piperidine may be used or a salt of a weak acid, such as acetic acid and benzoic acid, or a weak base, such as pyridine, amine and aniline, may be used alone. Preferably, a mixture of acetic acid and piperidine is used.

The product may be reacted with the compound of the formula 6 in the presence of a base, in order to obtain the compound of the formula 1, in which R is not H. In this reaction, dimethylformamide (DMF), tetrahydrofuran (THF), acetone, water or other organic solvent may be used. Preferably, dimethylformamide (DMF) or tetrahydrofuran (THF) is used as a solvent. For the base, an inorganic base, such as potassium carbonate, sodium carbonate, sodium hydroxide, potassium hydroxide and cesium carbonate, or an organic base, such as triethylamine and pyridine, may be used. Preferably, potassium carbonate or sodium carbonate is used.

The present invention also provides an anticancer agent comprising the 5-(1,3-diaryl-1H-pyrazol-4-ylmethylene)-thiazolidine-2,4-dione derivative represented by the formula 1 or a pharmaceutically acceptable salt thereof as an active ingredient.

Since the 5-(1,3-diaryl-1H-pyrazol-4-ylmethylene)-thiazolidine-2,4-dione derivative of the formula 1 has inhibitory activity against the CDC25B phosphatase, which plays a critical role in G2/M phase transition during cell division, it effectively inhibits cell division. Also, it has selectivity for other phosphatases in the human body and has been confirmed to effectively destroy human cancer cells in a xenografted nude mouse.

Therefore, an anticancer agent or a pharmaceutical composition comprising the compound of the formula 1 as an active ingredient may be prepared into an oral administration formulation, such as tablets, capsules, troches, syrup and emulsions, by adding a pharmaceutically acceptable, non-toxic carrier, a modifier, a filler, etc.

Administration dosage of the compound of the formula 1 may differ depending on the age, body weight, sex or health condition of the patient, administration type, and severity of disease. A dosage of 10 to 400 mg/day is normally acceptable for an adult with body weight of about 70 kg. The compound may be administered once or several times a day, as prescribed by a physician or a pharmacist.

Hereinafter, the present invention is described in further detail via the accompanying examples. However, the following examples are only for the understanding of the present invention and they should not be construed as limiting the scope of the present invention.

EXAMPLE 1

Preparation of 5-[3-(3,5-difluoro-phenyl)-1-phenyl-1H-pyrazol-4-ylmethylene]-thiazolidine-2,4-dione (Compound No. 58)

(1) Preparation of (3',5'-difluoromethoxy) acetophenone (Formula 2)

(3',5'-Dihydroxy) acetophenone (1.00 g, 6.57 mmol) was dissolved in 30 mL of anhydrous dimethylformamide. Potassium carbonate (2.00 g, 14.45 mmol) and potassium iodide (10.91 mg, $6.57 \times 10^{-2}$ mmol) were added and refluxed for 1 hour at 80° C. After cooling to 55-60° C., methyl chlorodifluoroacetate (1.75 mL, 16.43 mmol) was slowly added dropwise and the mixture was stirred for 30 minutes. After the reflux at 70-80° C. for 3 hours, the mixture was slowly cooled to room temperature. Ethyl acetate (30 mL) was added and the mixture was washed with water (10 mL×2 times). The organic layer was further washed 2 N hydrochloric acid solution (10 mL×3 times) and brine (10 mL×2 times). The organic layer was separated, dried with anhydrous magnesium sulfate, filtered and concentrated under reduced pressure. The residue was purified by silica gel chromatography (n-hexane/ethyl acetate=10:1) to obtain 1.13 g (68%) of the target product.

$^1$H NMR (200 MHz, CDCl$_3$) δ 2.61 (s, 3H), 6.58 (t, 2H, J=74 Hz), 7.14 (s, 1H), 7.55 (s, 1H).

(2) Preparation of phenylhydrazone of (3',5'-difluoromethoxy) acetophenone (Formula 4)

(3',5'-Difluoromethoxy) acetophenone (1.0 g, 3.97 mmol) was dissolved in 20 mL of anhydrous ethanol. Phenylhydrazine (0.39 mL, 3.97 mmol) and glacial acetic acid (11.00 µL, 0.20 mmol), a catalyst, were added and the mixture was stirred for 3 hours at room temperature. Ethyl acetate (20 mL) was added and the mixture was washed with water (10 mL×3 times) and brine (10 mL×2 times). The organic layer was dried with magnesium sulfate anhydrous, filtered and concentrated under reduced pressure to obtain 1.29 g (95%) of the target product.

(3) Preparation of 3-(3',5'-difluoromethoxy-phenyl)-1-phenyl-1H-pyrazol-4-carboxylaldehyde (Formula 5)

Phosphorus oxychloride (0.45 mL, 7.02 mol) was added to 2 mL of anhydrous dimethylformamide and the mixture was stirred for 1 hour at 0° C. Phenylhydrazone of (3',5'-difluoromethoxy) acetophenone (1.2 g, 3.51 mmol) dissolved in 5 mL of anhydrous dimethylformamide was slowly added dropwise and the mixture was stirred at 70-80° C. for 6 hours. After cooling to 0° C. with ice water, 30% sodium hydroxide solution was slowly added dropwise to adjust the pH to 7-8. The resultant solid was filtered and washed with water (10 mL×3 times). The filtered solid was dried to obtain 0.94 g (70%) of the target product.

$^1$H NMR (200 MHz, CDCl3) δ 6.63 (t, 2H, J=74 Hz), 7.02 (s, 1H), 7.44 (d, 1H, J =7.5 Hz), 7.54 (t, 2H, J=7.8 Hz), 7.63 (s, 2H), 7.79 (d, 2H, J=8.1 Hz), 8.55 (s, 1H), 10.06 (s, 1H).

(4) Preparation of 5-[3-(3,5-difluoro-phenyl)-1-phenyl-1H-pyrazol-4-ylmethylene]-thiazolidine-2,4-dione (Compound No. 58)

3-(3,5-Difluoromethoxy-phenyl)-1-phenyl-1H-pyrazol-4-carboxylaldehyde (0.50 g, 1.31 mmol) and thiazolidine-2,4-dione (153.00 mg, 1.31 mmol) were added 20 mL of anhydrous toluene. Glacial acetic acid (3.70 µL, $6.55 \times 10^{-2}$ mmol) and piperidine (7.80 µL, $7.86 \times 10^{-2}$ mmol) were added as catalyst and refluxed for 12 hours while removing water using a Dean-Stark trap. After cooling down to room temperature, stirring was performed for 6 hours. The resultant solid was filtered and washed with diethyl ether (10 mL×3 times). The filtered solid was dried to obtain 0.56 g (89%) of the target product.

$^1$H NMR (200 MHz, CDCl$_3$) δ 7.24 (t, 2H, J=74 Hz), 7.37 (s, 1H), 7.41-7.55 (m, 2H), 7.61 (t, 2H, J=2.8 Hz), 8.06 (d, 2H, J=7.2 Hz), 8.79 (s, 1H), 12.61 (br, 1H, NH).

EXAMPLE 2

Preparation of 5-[3-(3,5-difluoro-phenyl)-1-phenyl-1H-pyrazol-4-ylmethylene]-3-methyl-thiazolidine-2,4-dione (Compound No. 59)

5-[3-(3,5-Difluoro-phenyl)-1-phenyl-1H-pyrazol-4-ylmethylene]-thiazolidine-2,4-dione (Compound No. 58, 0.10 g, 0.21 mmol) was dissolved in 1.0 mL of anhydrous dimethylformamide. Sodium carbonate (26.50 mg, 0.25 mmol) was added under nitrogen atmosphere and iodomethane (20.00 µL, 0.32 mmol) was added 10 minutes later. The mixture was stirred for 2 hours at room temperature. Water was added after the reaction was completed. The resultant solid was washed with water (10 mL×3 times). The solid was dried to obtain 90.0 mg (87%) of the target product.

$^1$H NMR (200 MHz, CDCl$_3$) δ 3.26 (s, 3H), 6.61 (t, 2H, J=74 Hz), 7.03 (s, 1H), 7.30 (s, 1H), 7.42 (t, 1H, J=7.4 Hz), 7.54 (t, 2H, J=7.8 Hz), 7.78 (d, 2H, J=8.1 Hz), 7.87 (s, 1H), 8.19 (s, 1H).

EXAMPLE 3

Preparation of 5-[3-(3,5-difluoro-phenyl)-1-phenyl-1H-pyrazol-4-ylmethylene]-3-ethyl-thiazolidine-2,4-dione (Compound No. 60)

5-[3-(3,5-Difluoro-phenyl)-1-phenyl-1H-pyrazol-4-ylmethylene]-thiazolidine-2,4-dione (Compound No. 58, 0.10 g, 0.21 mmol) was dissolved in 1.0 mL of anhydrous dimethylformamide. Sodium carbonate (26.5 mg, 0.25 mmol) was added under nitrogen atmosphere and ethyl bromide (23.90 µL, 0.32 mmol) was added 10 minutes later. The mixture was stirred for 4 hours at room temperature. Water was added after the reaction was completed. The resultant solid was washed with water (10 mL×3 times). The solid was dried to obtain 85.3 mg (80%) of the target product.
$^1$H NMR (200 MHz, CDCl$_3$) δ 1.29 (t, 3H, J=7.5 Hz), 3.83 (q, 2H, J=7.0 Hz), 6.61 (t, 2H, J=74 Hz), 7.03 (s, 1H), 7.31 (s, 1H), 7.42 (t, 1H, J=7.5 Hz), 7.54 (t, 2H, J=7.5 Hz), 7.79 (d, 2H, J=9.0 Hz), 7.86 (s, 1H), 8.19 (s, 1H).

EXAMPLE 4

Preparation of 5-[3-(3-bromo-4-ethoxy-phenyl)-1-phenyl-1H-pyrazol-4-ylmethylene]-thiazolidine-2,4-dione (Compound No. 77)

(1) Preparation of phenylhydrazone of (3'-bromo-4'-ethoxy) acetophenone (Formula 4)

(3'-Bromo-4'-ethoxy) acetophenone (4.00 g, 16.45 mmol) was dissolved in 100 mL of anhydrous ethanol. Phenylhydrazine (2.14 g, 19.75 mmol) and glacial acetic acid (9.16 µL, 0.16 mmol), a catalyst, was added and the mixture was stirred at room temperature for 5 hours. When the reaction was completed, 50 mL of ethyl acetate was added and the solution was extracted with 2 N hydrochloric acid solution (30 mL×3 times) and washed with brine (30 mL×2 times). The organic layer was dried with anhydrous magnesium sulfate to obtain 3.9 g (74.3%) of the target product in white solid form.

(2) Preparation of 3-(3-bromo-4-ethoxy-phenyl)-1-phenyl-1H-pyrazol-4-carboxylaldehyde (Formula 5)

Phosphorus oxychloride (3.13 mL, 33.6 mmol) was added to 2 mL of anhydrous dimethylformamide and the mixture was stirred at 0° C. under nitrogen atmosphere for 1 hour. Phenylhydrazone of (3'-bromo-4'-ethoxy)acetophenone (3.90 g, 11.7 mmol) dissolved in 5 mL of anhydrous dimethylformamide was slowly added dropwise and the mixture was stirred for 6 hours at 70-80° C. After cooling to 0° C. with ice water, 30% sodium hydroxide solution was slowly added dropwise to adjust the pH to 7-8. The resultant solid was washed with water (10 mL×3 times) and dried to obtain 2.10 g (48.4%) of the target product.
$^1$H NMR (300 MHz, CDCl$_3$) δ 1.52 (t, 3H, J=6.92 Hz), 4.19 (q, 2H, J=6.92 Hz), 7.0 (d, 1H, J=8.55 Hz), 7.4-8.15 (m, 7H), 8.52 (s, 1H), 10.04 (s, 1H).

(3) Preparation of 5-[3-(3-bromo-4-ethoxy-phenyl)-1-phenyl-1H-pyrazol-4-ylmethylene]-thiazolidine-2,4-dione (Compound No. 77)

3-(3-Bromo-4-ethoxy-phenyl)-1-phenyl-1H-pyrazol-4-carboxylaldehyde (0.50 g, 1.35 mmol) and thiazolidine-2,4-dione (158.40 mg, 1.35 mmol) were added to 20 mL of anhydrous toluene. Glacial acetic acid (3.81 µL, 6.75×10$^{-2}$ mmol) and piperidine (8.04 µL, 8.10×10$^{-2}$ mmol) were added as catalyst and reflux was performed for 3 hours while removing water using a Dean-Stark trap. After cooling to room temperature, the mixture was stirred for 6 hours. The resultant solid was washed with diethyl ether (10 mL×3 times) and dried to obtain 0.52 g (82%) of the target product.

EXAMPLE 5

Preparation of 5-[3-(3-bromo-4-ethoxy-phenyl)-1-phenyl-1H-pyrazol-4-ylmethylene]-3-methyl-thiazolidine-2,4-dione (Compound No. 78)

5-[3-(3-Bromo-4-ethoxy-phenyl)-1-phenyl-1H-pyrazol-4-yl-methylene]-thiazolidine-2,4-dione (Compound No. 77, 0.10 g, 0.21 mmol) was dissolved in 1.00 mL of anhydrous dimethylformamide. Sodium hydride (12.74 mg, 0.32 mmol) was added under nitrogen atmosphere and iodomethane (19.78 µL, 0.32 mmol) was added 5 minutes later. The mixture was stirred at room temperature for 2 hours. When the reaction was completed, 10 mL of water was added and the solution was extracted with dichloromethane (10 mL×2 times). The organic layer was washed with brine and dried with anhydrous magnesium sulfate. The solvent was removed under reduced pressure. The product was purified with silica gel chromatography (n-hexane/ethyl acetate=4:1) to obtain 48 mg (46.7%) of the target product in yellow solid form.
$^1$H NMR (300 MHz, CDCl$_3$) δ 1.53 (t, 3H, J=7.2 Hz), 3.25 (s, 3H), 4.19 (q, 2H, J=7.0 Hz), 7.0 (d, 1H, J=8.4 Hz), 7.39-7.55 (m, 4H), 7.78 (d, 2H, J=7.8 Hz), 7.92 (d, 2H, J=2.1 Hz), 8.17 (s, 1H).

EXAMPLE 6

Preparation of 5-[3-(3-bromo-4-ethoxy-phenyl)-1-phenyl-1H-pyrazol-4-ylmethylene]-3-ethyl-thiazolidine-2,4-dione (Compound No. 79)

5-[3-(3-Bromo-4-ethoxy-phenyl)-1-phenyl-1H-pyrazol-4-yl-methylene]-thiazolidine-2,4-dione (Compound No. 77, 0.10 mg, 0.21 mmol) was dissolved in 1.00 mL of anhydrous dimethylformamide. Sodium hydride (12.74 mg, 0.32 mmol) was added under nitrogen atmosphere and bromoethane (23.72 µL, 0.32 mmol) was added 5 minutes later. The mixture was stirred at room temperature for 2 hours. When the reaction was completed, 10 mL of water was added and the solution was extracted with dichloromethane (10 mL×2 times). The organic layer was washed with brine and dried with anhydrous magnesium sulfate. The solvent was removed under reduced pressure. The product was purified with silica gel chromatography (n-hexane/ethyl acetate=4:1) to obtain 52 mg (49.2%) of the target product in yellow solid form.
$^1$H NMR (300 MHz, CDCl$_3$) δ 1.28 (t, 3H, J=7.2 Hz), 1.53 (t, 3H, J=7.1 Hz), 3.82 (q, 2H, J=7.2 Hz), 4.18 (q, 2H, J=6.9 Hz), 7.00 (d, 1H, J=8.7 Hz), 7.39 (t, 1H, J=7.4 Hz), 7.49-7.55 (m, 3H), 7.78 (d, 2H, J=7.8 Hz), 7.89 (d, 2H, J=16.8 Hz), 8.16 (s, 1H).

The compounds given in Table 1a-1p below were prepared in the manner similar to as in Examples 1-6.

TABLE 1a

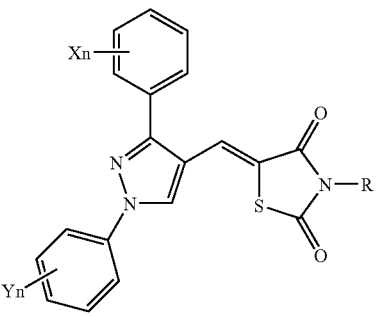

(1)

| Comp. No. | Xn | Yn | R | ¹HNMR(DMSO-$d_6$) δ |
|---|---|---|---|---|
| 1 | 2-Cl | H | H | 7.17 (s, 1 H), 7.19-8.02 (m, 9 H), 8.74 (s, 1 H), 12.51 (br, 1 H, NH) |
| 2 | 2-Cl | H | Et | 1.26 (t, 3 H, J = 7.2 Hz), 3.80 (q, 2 H, J = 7.0 Hz), 7.26 (s, 1 H), 7.39-7.82 (m, 9 H), 8.19 (s, 1 H) |
| 3 | 3-Br | H | H | 7.38-8.00 (m, 10 H), 8.68 (s, 1 H), 12.53 (br, 1 H, NH) |
| 4 | 2-Br | H | H | 7.17 (s, 1 H), 7.46-8.03 (m, 9 H), 8.74 (s, 1 H), 12.52 (br, 1 H, NH) |
| 5 | 2-Br | H | Et | 1.26 (t, 3 H, J = 7.1 Hz), 3.79 (q, 2 H, J = 7.1 Hz), 7.26 (s, 1 H), 7.36-7.82 (m, 9 H), 8.19 (s, 1 H) |
| 6 | 3-OMe | H | H | 3.84 (s, 3 H), 7.09-7.20 (m, 3 H), 7.40-7.60 (m, 5 H), 8.02 (d, 2 H, J = 8.4 Hz) 8.70 (s, 1 H), 12.54 (br, 1 H, NH) |
| 7 | 2-OMe | H | H | 3.84 (s, 3 H), 7.09-7.58 (m, 6 H), 7.99 (d, 2 H, J = 9.6 Hz) 8.64 (s, 1 H), 12.47 (br, 1 H, NH) |
| 8 | 2-OMe | H | Me | 3.23 (s, 3 H), 3.84 (s, 3 H), 7.03-54 (m, 7 H), 7.70 (s, 1 H), 7.79 (d, 2 H, J = 7.1 Hz), 8.16 (s, 1 H) |
| 9 | 4-OMe | H | H | 1.37 (t, 3 H, J = 7.1 Hz), 4.11 (q, 2 H, J = 7.0 Hz), 7.10 (d, 1 H, J = 9.0 Hz), |

TABLE 1a-continued

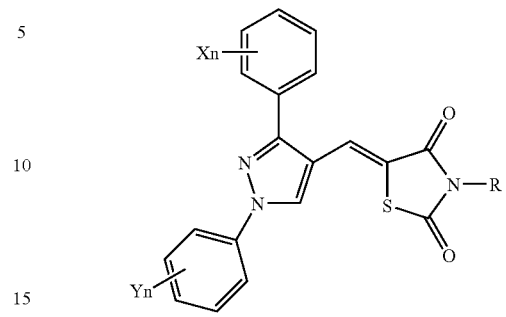

(1)

| Comp. No. | Xn | Yn | R | ¹HNMR(DMSO-$d_6$) δ |
|---|---|---|---|---|
|  |  |  |  | 7.40-7.02 (m, 9 H), 8.66 (s, 1 H), 12.5 (br, 1 H, NH) |
| 10 | 3-Et | H | H | 1.45 (t, 3 H, J = 7.5 Hz), 2.92 (q, 2 H, J = 7.5 Hz), 7.57-7.81 (m, 8 H), 8.23 (d, 2 H, J = 7.8 Hz), 8.91 (s, 1 H), 12.74 (br, 1 H, NH) |
| 11 | 2-NO$_2$ | H | H | 7.23 (s, 1 H), 7.38-8.10 (m, 9 H), 8.73 (s, 1 H), 12.52 (br, 1 H, NH) |
| 12 | 2-NO$_2$ | H | Me | 3.24 (s, 3 H), 7.22 (s, 1 H), 7.38-8.10 (m, 9 H), 8.73 (s, 1 H) |
| 13 | 2-NO$_2$ | H | Et | 1.36 (t, 3 H, J = 7.1 Hz), 4.05 (q, 2 H, J = 7.0 Hz), 7.22 (s, 1 H), 7.38-8.10 (m, 9 H), 8.73 (s, 1 H) |
| 14 | 3-NO$_2$ | H | H | 3.89 (s, 3 H), 7.11-7.60 (m, 8 H), 8.00 (d, 2 H, J = 8.2 Hz), 8.67 (s, 1 H), 12.55 (br, 1 H, NH) |
| 15 | 3-NO$_2$ | H | Me | 3.26 (s, 3 H), 7.27-8.60 (m, 11 H) |
| 16 | 3-CF$_3$ | H | H | 7.64-8.28 (m, 10 H), 8.89 (s, 1 H), 12.80 (br, 1 H, NH) |
| 17 | 3-CF$_3$ | H | Me | 3.60 (s, 3 H), 7.64-8.28 (m, 10 H), 8.98 (s, 1 H) |

TABLE 1b

| Comp. No. | Xn | Yn | R | ¹H NMR(CDCl$_3$) |
|---|---|---|---|---|
| 18 | 2-CF$_3$ | H | H | 7.10 (s, 1H), 7.40-8.01 (m, 9H), 8.76 (s, 1H), 12.52 (br, 1H, NH) |
| 19 | 2-CF$_3$ | H | Me | 3.21 (s, 3H), 7.39-7.87 (m, 10H), 8.12 (s, 1H) |
| 20 | 2,5-di(Cl) | H | H | 7.19 (s, 1H), 7.41-7.75 (m, 6H), 8.01 (d, 2H, J = 7.8 Hz) 8.76 (s, 1H), 12.54 (br, 1H, NH) |
| 21 | 3,4-di(OMe) | H | H | 3.84 (s, 6H), 7.22-8.03 (m, 9H), 8.66 (s, 1H), 12.50 (br, 1H, NH) |
| 22 | 3,5-di(OMe) | H | H | 3.81 (s, 6H), 6.62-6.77 (m, 3H), 7.34-7.45 (m, 1H), 7.51-7.62 (m, 3H), 8.00 (d, 2H, J = 8.1 Hz), 8.68 (s, 1H), 12.51 (br, 1H, NH) |
| 23 | 3,5-di(OMe) | H | Me | 3.24 (s, 3H), 3.86 (s, 6H), 6.57 (t, 1H, J = 2.2 Hz), 6.78 9d, 2H, J = 2.2 Hz), 7.46-7.88 (m, 4H), 8.17 (s, 1H) |
| 24 | 2.5-di(OMe) | H | H | 3.76 (s, 3H), 3.81 (s, 3H), 7.03-8.07 (m, 9H), 8.09 (s, 1H), 12.53 (br, 1H, NH) |
| 25 | 3,5-di(OPr) | H | H | 1.02 (t, 4H, J = 7.3 Hz), 1.71-1.85 (m, 4H), 4.02 (t, 4H, J = 5.9 Hz), 6.66 (d, 1H, J = 2.4 Hz), 6.75 (s, 2H), 7.47 (d, 1H, J = 6.5 Hz), 7.54-7.67 (m, 3H), 8.04 (d, 2H, J = 8.1 Hz), 8.70 (s, 1H), 12.50 (br, 1H, NH) |
| 26 | 3,5-di(OPr) | H | Me | 1.02 (t, 4H, J = 7.3 Hz), 1.71-1.85 (m, 4H), 3.25 (s, 1H), 4.02 (t, 4H, J = 5.9 Hz), 6.66 (d, 1H, J = 2.4 Hz), 6.75 (s, 2H), 7.47 (d, 1H, J = 6.5 Hz), 7.54-7.67 (m, 3H), 8.04 (d, 2H, J = 8.1 Hz), 8.70 (s, 1H), 12.50 (br, 1H, NH) |
| 27 | 3,5-di(OPr) | H | Et | 1.02 (t, 4H, J = 7.3 Hz), 1.37 (t, 3H, J = 7.1 Hz), 1.71-1.85 (m, 4H), 3.81 (q, 2H, J = 7.1 Hz), 4.02 (t, 4H, J = 5.9 Hz), 6.66 (d, 1H, J = |

TABLE 1b-continued

| Comp. No. | Xn | Yn | R | ¹H NMR(CDCl₃) |
|---|---|---|---|---|
| | | | | 2.4 Hz), 6.75 (s, 2H), 7.47 (d, 1H, J = 6.5 Hz), 7.54-7.67 (m, 3H), 8.04 (d, 2H, J = 8.1 Hz), 8.70 (s, 1H), 12.48 (br, 1H, NH) |
| 28 | 3,5-di(OPr) | H | | 1.02 (t, 4H, J = 7.3 Hz), 1.71-1.89 (m, 4H), 4.02 (t, 4H, J = 5.9 Hz), 4.19 (d, 2H, J = 23.9 Hz), 5.17 (d, 2H, J = 9.0 Hz), 5.77-5.91 (m, 1H), 6.66 (d, 1H, J = 2.4 Hz), 6.75 (s, 2H), 7.47 (d, 1H, J = 6.5 Hz), 7.54-7.67 (m, 3H), 8.04 (d, 2H, J = 8.1 Hz), 8.70 (s, 1H), 11.80 (br, 1H, NH) |
| 29 | 3,5-di(OPr) | H | | 1.05 (t, 6H, J = 7.4 Hz), 1.73-1.94 (m, 4H), 2.24-2.30 (m, 1H), 3.97 (t, 4H, J = 6.5 Hz), 4.50 (d, 2H, J = 2.4 Hz), 6.54-6.60 (m, 1H), 6.73-6.78 (m, 2H), 7.37-7.58 (m, 3H), 7.76-7.84 (m, 2H), 8.02 (s, 1H), 8.18 (s, 1H) |
| 30 | 3,5-di(O—Pr$^i$) | H | H | 1.30 (d, 12H, J = 6.0 Hz), 4.64-4.72 (m, 2H), 6.59 (s, 1H), 7.43 (d, 1H, J = 7.2 Hz), 7.52-7.65 (m, 3H), 8.01 (d, 2H, J = 8.4 Hz), 8.68 (s, 1H), 12.52 (br, 1H, NH) |
| 31 | 3,5-di(O—Pr$^i$) | H | Me | 1.37 (d, 12H, J = 6.7 Hz), 3.25 (s, 1H), 4.51-4.67 (m, 2H), 6.54 (t, 1H, J = 2.2 Hz), 6.74 (d, 2H, J = 2.2 Hz), 7.35-7.84 (m, 5H), 7.98 (s, 1H), 8.17 (s, 1H) |

TABLE 1c

| Comp. No. | Xn | Yn | R | ¹H NMR(CDCl₃) |
|---|---|---|---|---|
| 32 | 3,5-di(O—Pr$^i$) | H | Et | 1.37 (t, 3 H, J = 7.1 Hz), 1.60 (d, 12 H, J = 6.1 Hz), 3.81 (q, 2 H, J = 7.1 Hz), 4.51-4.68 (m, 2 H), 6.51-6.56 (m, 1 H), 6.72-6.77 (m, 2 H), 7.37 (t, 1 H, J = 7.3 Hz), 7.45-7.57 (m, 2 H), 7.78 (d, 2 H, J = 7.7 Hz), 7.96 (s, 1 H), 8.17 (s, 1 H) |
| 33 | 3,5-di(O—Pr$^i$) | H | allyl | 1.30 (d, 12 H, J = 6.0 Hz), 4.19 (d, 2 H, J = 23.9 Hz), 4.64-4.72 (m, 2 H), 5.17 (d, 2 H, J = 9.0 Hz), 5.77-5.91 (m, 1 H), 6.59 (s, 1 H), 7.43 (d, 1 H, J = 7.2 Hz), 7.52-7.65 (m, 3 H), 8.01 (d, 2 H, J = 8.4 Hz), 8.68 (s, 1 H), 12.52 (br, 1 H, NH) |
| 34 | 3,5-di(O—Pr$^i$) | H | propargyl | 1.37 (d, 12 H, J = 6.1 Hz), 2.24-2.31 (m, 1 H), 4.50 (d, 2 H, J = 2.4 Hz), 4.52-4.68 (m, 2 H), 6.53 (q, 1 H, J = 2.2 Hz), 6.71-6.78 (m, 2 H), 7.33-7.87 (m, 5 H), 8.01 (s, 1 H), 8.17 (s, 1 H) |
| 35 | 3,5-di(O-cyclopropylmethyl) | H | H | 0.37 (q, 4 H, J = 4.9 Hz), 0.62 (q, 4 H, J = 6.1 Hz), 1.20-1.34 (m, 2 H), 2.93 (d, 4 H, J = 6.9 Hz), 6.66 (s, 1 H), 6.74 (s, 2 H), 7.45 (t, 1 H, J = 7.3 Hz), 7.60 (t, 3 H, J = 8.9 Hz), 8.05 (d, 2 H, J = 7.7 Hz), 8.71 (s, 1 H), 12.56 (s, 1 H, NH). |
| 36 | 3,5-di(O-cyclopropylmethyl) | H | Me | 0.36 (q, 4 H, J = 6.1 Hz), 0.64 (q, 4 H, J = 6.2 Hz), 1.20-1.40 (m, 2 H), 3.25 (s, 3 H), 3.85 (d, 4 H, J = 6.9 Hz), 6.58 (s, 1 H), 6.76 (s, 2 H), 7.40 (d, 4 H, J = 7.3 Hz), 7.52 (t, 2 H, J = 4.5 Hz), 7.79 (d, 2 H, J = 8.1 Hz), 7.96 (s, 1 H), 8.17 (s, 1 H). |
| 37 | 3,5-di(O-cyclopropylmethyl) | H | Et | 0.36 (q, 4 H, J = 5.2 Hz), 0.66 (q, 4 H, J = 6.2 Hz), 0.78-0.94 (m, 2 H), 1.28 (t, 3 H, J = 7.1 Hz), 3.81 (q, 2 H, J = 6.9 Hz), 3.85 (d, 4 H, J = 7.3 Hz), 6.58 (s, 1 H), 6.76 (s, 2 H), 7.38 (t, 1 H, J = 7.3 Hz), 7.52 (t, 2 H, J = 7.7 Hz), 7.79 (d, 2 H, J = 8.5 Hz), 7.95 (s, 1 H), 8.16 (s, 1 H). |
| 38 | 3,5-di(O-cyclopropylmethyl) | H | Pr | 0.36 (q, 4 H, J = 4.9 Hz), 0.67 (q, 4 H, J = 4.2 Hz), 0.96 (t, 3 H, J = 7.3 Hz), 1.60-1.81 (m, 2 H), 3.72 (t, 2 H, J = 7.3 Hz), 3.85 (d, 4 H, J = 6.9 Hz), 6.58 (s, 1 H), 6.77 (s, 2 H), 7.38 (t, 1 H, J = 7.1 Hz), 7.52 (t, 2 H, J = 7.5 Hz), 7.78 (d, 2 H, J = 8.1 Hz), 7.94 (s, 1 H), 8.17 (s, 1 H). |

TABLE 1c-continued

| Comp. No. | Xn | Yn | R | $^1$H NMR(CDCl$_3$) |
|---|---|---|---|---|
| 39 | 3,5-di(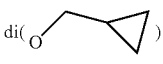) | H |  | 0.36 (q, 4 H, J = 5.0 Hz), 0.65 (q, 4 H, J = 6.2 Hz), 1.20-1.32 (m, 2 H), 3.84 (d, 4 H, J = 6.9 Hz), 4.34 (d, 1 H, J = 5.9 Hz), 5.29 (dd, 2 H, J = 10.2 Hz, 17.2 Hz), or 5.26 (d, 1 H, J = 10.23 Hz), 5.29 (d, 1 H, J = 17.2 Hz), 5.76-5.93 (m, 1 H), 6.58 (s, 1 H), 6.75 (s, 2 H), 7.38 (t, 1 H, J = 7.4 Hz), 7.52 (t, 2 H, J = 7.8 Hz), 7.79 (d, 2 H, J = 8.1 Hz), 7.95 (s, 1 H), 8.17 (s, 1 H). |
| 40 | 3,5-di() | H |  | 0.36 (q, 4 H, J = 5.1 Hz), 0.66 (q, 4 H, J = 6.2 Hz), 1.20-1.38 (m, 2 H), 2.28 (s, 1 H), 3.85 (d, 4 H, J = 6.9 Hz), 4.50 (s, 1 H), 6.58 (s, 1 H), 6.76 (s, 2 H), 7.39 (t, 1 H, J = 7.5 Hz), 7.52 (t, 2 H, J = 7.5 Hz), 7.79 (d, 2 H, J = 7.8 Hz), 8.00 (s, 1 H), 8.17 (s, 1 H). |
| 41 | 3,5-di(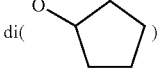) | H | H | 1.50-2.05 (m, 16 H), 4.80-4.94 (m, 2 H), 6.53 (s, 1 H), 6.68 (s, 2 H), 7.42 (t, 1 H, J = 7.4 Hz), 7.57 (t, 2 H, J = 7.8 Hz), 7.64 (s, 1 H), 8.01 (d, 2 H, J = 7.8 Hz), 8.67 (s, 1 H), 12.52 (br, 1 H, NH). |

TABLE 1d

| Comp. No. | Xn | Yn | R | $^1$H NMR(CDCl$_3$) |
|---|---|---|---|---|
| 42 | 3,5-di(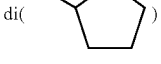) | H | Me | 1.52-1.97 (m, 16 H), 3.25 (s, 3 H), 4.71-4.54 (m, 2 H), 6.51 (s, 1 H), 6.72 (s, 2 H), 7.38 (t, 1 H, J = 7.3 Hz), 7.52 (t, 2 H, J = 7.9 Hz), 7.80 (d, 2 H, J = 7.7 Hz), 7.98 (s, 1 H), 8.17 (s, 1 H). |
| 43 | 3,5-di(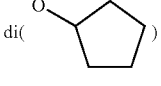) | H | Et | 1.24 (t, 3 H, J = 7.1 Hz), 1.53-1.97 (m, 16 H), 3.81 (q, 2 H, J = 7.1 Hz), 4.72-4.86 (m, 2 H), 6.50 (s, 1 H), 6.71 (s, 2 H), 7.37 (t, 1 H, J = 7.3 Hz), 7.51 (t, 2 H, J = 7.7 Hz), 7.80 (d, 2 H, J = 7.3 Hz), 7.97 (s, 1 H), 8.16 (s, 1 H). |
| 44 | 3,5-di(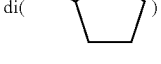) | H | Pr | 0.95 (t, 3 H, J = 7.3 Hz), 1.48-1.97 (m, 18 H), 3.72 (q, 2 H, J = 7.3 Hz), 4.72-4.85 (m, 2 H), 6.50 (s, 1 H), 6.71 (s, 2 H), 7.37 (t, 1 H, J = 7.3 Hz), 7.52 (t, 2 H, J = 7.5 Hz), 7.80 (d, 2 H, J = 8.5 Hz), 7.97 (s, 1 H), 8.17 (s, 1 H). |
| 45 | 3,5-di(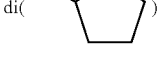) | H |  | 1.48-1.97 (m, 16 H), 2.71 (s, 1 H), 4.50 (s, 2 H), 4.73-4.87 (m, 2 H), 6.50 (s, 1 H), 6.71 (s, 2 H), 7.38 (t, 1 H, J = 7.3 Hz), 7.52 (t, 2 H, J = 7.5 Hz), 7.80 (d, 2 H, J = 7.9 Hz), 8.02 (s, 1 H), 8.17 (s, 1 H). |
| 46 | 3,4-di(O—CHF$_2$) | H | H | 7.20-7.34 (m, 2 H), 7.36 (t, 1 H, J = 3 Hz), 7.37 (t, 1 H, J = 73 Hz), 7.41-7.70 (m, 5 H), 8.06 (d, 2 H, J = 7.3 Hz), 8.77 (s, 1 H), 12.60 (s, 1 H, NH). |
| 47 | 3,4-di(O—CHF$_2$) | H | Me | 3.26 (s, 3 H), 6.61 (t, 2 H, J = 73 Hz), 6.62 (t, 2 H, J = 73 Hz), 7.35-7.68 (m, 6 H), 7.79 (d, 2 H, J = 7.3 Hz), 7.86 (s, 1 H), 8.19 (s, 1 H). |
| 48 | 3,4-di(O—CHF$_2$) | H | Et | 1.28 (t, 3 H, J = 7.1 Hz), 3.82 (q, 2 H, J = 7.2 Hz), 6.60 (t, 1 H, J = 73 Hz), or 6.62 (t, 1 H, J = 73 Hz), 7.30-7.90 (m, 9 H), 8.19 (s, 1 H). |
| 49 | 3,4-di(O—CHF$_2$) | H | Pr | 0.96 (t, 2 H, J = 7.5 Hz), 1.60-1.80 (m, 2 H), 3.73 (t, 2 H, J = 7.3 Hz), 6.60 (t, 1 H, J = 7.3 Hz), 6.62 (t, 1 H, J = 73 Hz), 7.33-7.90 (m, 9 H), 8.19 (s, 1 H). |
| 50 | 3,4-di(O—CHF$_2$) | H |  | 4.34 (d, 2 H, J = 5.9 Hz), 5.27 (d, 2 H, J = 10.2 Hz), 530 (d, 2 H, J = 22.0 Hz), or 5.30 (d, 2 H, J = 10.2 Hz, 22.0 Hz), 5.72-6.00 (m, 1 H), 6.60 (t, 1 H, J = 73 Hz), 6.62 (t, 1 H, J = 73 Hz), 7.33-7.78 (m, 6 H), 7.79 (d, 2 H, J = 7.3 Hz), 7.87 (s, 1 H), 8.20 (s, 1 H). |

TABLE 1d-continued

| Comp. No. | Xn | Yn | R | ¹H NMR(CDCl₃) |
|---|---|---|---|---|
| 51 | 3,4-di(O—CHF₂) | H | —CH₂—C≡CH | 2.29 (s, 1 H), 4.51 (s, 2 H), 6.61 (t, 1 H, J = 73 Hz), 6.62 (t, 1 H, J = 73 Hz), 7.40-7.57 (m, 6 H), 7.79 (d, 2 H, J = 7.7 Hz), 7.90 (s, 1 H), 8.20 (s, 1 H). |
| 52 | 3-(O—CH₂-cyclopropyl), 4-(O—CHF₂) | H | H | 0.37 (q, 2 H, J = 5.0 Hz), 0.59 (q, 2 H, J = 6.0 Hz), 1.21-1.31 (m, 1 H), 3.91 (d, 2 H, J = 6.9 Hz), 7.20 (t, 1 H, J = 73 Hz), 7.22-7.62 (m, 7 H), 8.03 (d, 2 H, J = 7.7 Hz), 8.71 (s, 1 H), 12.55 (s, 1 H, NH). |
| 53 | 3-(O—CH₂-cyclopropyl), 4-(O—CHF₂) | H | Me | 0.38 (q, 2 H, J = 5.9 Hz), 0.67 (q, 4 H, J = 6.5 Hz), 1.20-1.43 (m, 1 H), 3.25 (s, 3 H), 3.96 (d, 2 H, J = 6.9 Hz), 6.70 (t, 1 H, J = 75 Hz), 7.09-7.39 (m, 3 H), 7.43 (t, 1 H, J = 6.3 Hz), 7.53 (t, 2 H, J = 7.5 Hz), 7.80 (d, 2 H, J = 7.3 Hz), 7.90 (s, 1 H), 8.18 (s, 1 H). |
| 54 | 3-(O—CH₂-cyclopropyl), 4-(O—CHF₂) | H | Et | 0.39 (q, 2 H, J = 5.3 Hz), 0.67 (q, 4 H, J = 5.8 Hz), 1.20-1.39 (m, 4 H), 3.82 (q, 2 H, J = 7.1 Hz), 3.97 (d, 2 H, J = 6.9 Hz), 6.70 (t, 1 H, J = 75 Hz), 7.11-7.36 (m, 3 H), 7.42 (d, 1 H, J = 6.9 Hz), 7.53 (t, 2 H, J = 7.5 Hz), 7.79 (d, 2 H, J = 7.3 Hz), 7.89 (s, 1 H), 8.18 (s, 1 H). |

TABLE 1e

| Comp. No. | Xn | Yn | R | ¹H NMR(CDCl₃) |
|---|---|---|---|---|
| 55 | 3-(O—CH₂-cyclopropyl), 4-(O—CHF₂) | H | Pr | 0.38 (q, 2 H, J = 5.0 Hz), 0.67 (q, 4 H, J = 6.2 Hz), 0.96 (m, 1 H), 1.22-1.45 (m, 2 H), 3.72 (q, 2 H, J = 7.1 Hz), 3.96 (d, 2 H, J = 7.3 Hz), 6.70 (t, 1 H, J = 75 Hz), 7.12-7.36 (m, 3 H), 7.42 (d, 1 H, J = 7.7 Hz), 7.53 (t, 2 H, J = 7.9 Hz), 7.79 (d, 2 H, J = 8.1 Hz), 7.89 (s, 1 H), 8.18 (s, 1 H). |
| 56 | 3-(O—CH₂-cyclopropyl), 4-(O—CHF₂) | H | —CH₂—CH=CH₂ | 0.39 (q, 2 H, J = 5.1 Hz), 0.67 (q, 2 H, J = 6.2 Hz), 3.96 (d, 2 H, J = 7.3 Hz), 4.35 (d, 2 H, J = 5.7 Hz), 5.24 (d, 2 H, J = 10.2 Hz), 5.29 (d, 2 H, J = 27.9 Hz), 5.75-5.98 (m, 1 H), 6.70 (t, 1 H, J = 76 Hz), 7.18 (d, 2 H, J = 8.1 Hz), 7.18-7.33 (m, 2 H), 7.40 (d, 1 H, J = 8.1 Hz), 7.53 (t, 2 H, J = 7.8 Hz), 7.79 (d, 2 H, J = 7.8 Hz), 7.90 (s, 1 H), 8.18 (s, 1 H). |
| 57 | 3-(O—CH₂-cyclopropyl), 4-(O—CHF₂) | H | —CH₂—C≡CH | 0.38 (q, 2 H, J = 5.0 Hz), 0.67 (q, 2 H, J = 6.4 Hz), 1.20-1.43 (m, 1 H), 2.28 (s, 1 H), 3.96 (d, 2 H, J = 6.9 Hz), 4.51 (s, 2 H), 6.70 (t, 1 H, J = 75 Hz), 7.06-7.34 (m, 3 H), 7.43 (t, 1 H, J = 7.3 Hz), 7.54 (t, 2 H, J = 7.7 Hz), 7.79 (d, 2 H, J = 7.7 Hz), 7.94 (s, 1 H), 8.18 (s, 1 H). |
| 58 | 3,5-di(O—CHF₂) | H | H | 7.24 (t, 2 H, J = 74 Hz), 7.37 (s, 1 H), 7.41-7.55 (m, 2 H), 7.61 (t, 2 H, J = 2.8 Hz), 8.06 (d, 2 H, J = 7.2 Hz), 8.79 (s, 1 H), 12.61 (br, 1 H, NH) |
| 59 | 3,5-di(O—CHF₂) | H | Me | 3.26 (s, 3 H), 6.61 (t, 2 H, J = 74 Hz), 7.03 (s, 1 H), 7.30 (s, 1 H), 7.42 (t, 1 H, J = 7.4 Hz), 7.54 (t, 2 H, J = 7.8 Hz), 7.78 (d, 2 H, J = 8.1 Hz), 7.87 (s, 1 H), 8.19 (s, 1 H) |
| 60 | 3,5-di(O—CHF₂) | H | Et | 1.29 (t, 3 H, J = 7.5 Hz), 3.83 (q, 2 H, J = 7.0 Hz), 6.61 (t, 2 H, J = 74 Hz), 7.03 (s, 1 H), 7.31 (s, 1 H), 7.42 (t, 1 H, J = 7.5 Hz), 7.54 (t, 2 H, J = 7.5 Hz), 7.79 (d, 2 H, J = 9.0 Hz), 7.86 (s, 1 H), 8.19 (s, 1 H) |
| 61 | 3,5-di(O—CHF₂) | H | Pr | 0.96 (t, 3 H, J = 7.4 Hz), 1.64-1.79 (m, 2 H), 3.73 (t, 2 H, J = 7.3 Hz), 6.61 (t, 1 H, J = 73 Hz), 7.02 (s, 1 H), 7.30 (s, 2 H), 7.43 (t, 1 H, J = 7.1 Hz), 7.54 (t, 2 H, J = 7.5 Hz), 7.79 (d, 2 H, J = 7.9 Hz), 7.85 (s, 1 H), 8.19 (s, 1 H). |

TABLE 1e-continued

| Comp. No. | Xn | Yn | R | $^1$H NMR(CDCl$_3$) |
|---|---|---|---|---|
| 62 | 3,5-di(OCH$_2$C$_6$H$_5$) | H | H | 5.17 (s, 4 H), 6.85 (s, 3 H), 7.32 (m, 14 H), 8.01 (d, 2 H, J = 8.4 Hz), 8.69 (s, 1 H), 12.54 (br, 1 H, NH). |
| 63 | 3,5-di(OCH$_2$C$_6$H$_5$) | H | Me | 3.25 (s, 3 H), 5.10 (s, 4 H), 7.19-8.07 (m, 19 H), 8.60 (s, 1 H), 8.76 (s, 1 H), 12.63 (br, 1 H, NH). |
| 64 | 3,5-di(OCH$_2$C$_6$H$_5$) | H | Et | 1.28 (t, 3 H, J = 7.2 Hz), 3.82 (q, 2 H, J = 7.3 Hz), 5.10 (s, 4 H), 6.71-6.90 (m, 3 H), 7.32-7.52 (m, 14 H), 7.79 (d, 2 H, J = 7.8 Hz), 7.96 (s, 1 H), 8.17 (s, 1 H). |
| 65 | 3,5-di(OCH$_2$C$_6$H$_5$) | 2-Me-4-NO$_2$-C$_6$H$_3$ | H | 5.21 (s, 4 H), 6.92 (s, 3 H), 7.34 (m, 9 H), 7.64 (s, 1 H), 8.42 (q, 4 H, J = 9.2 Hz), 8.94 (s, 1 H), 12.62 (br, 1 H, NH). |

TABLE 1f

| Comp. No. | Xn | Yn | R | $^1$H NMR(CDCl$_3$) |
|---|---|---|---|---|
| 66 | 3-Cl, 2-(OMe) | H | H | 3.30 (s, 3 H), 7.54-7.99 (m, 9 H), 8.67 (s, 1 H), 12.43 (br, 1 H, NH), 11.12 (br, 1 H, NH) |
| 67 | 3-Cl, 2-(OEt) | H | H | 1.41 (t, 3 H, J = 6.7 Hz), 4.21 (q, 2 H, J = 6.9 Hz), 7.54-7.99 (m, 9 H), 8.67 (s, 1 H), 12.43 (br, 1 H, NH), 11.12 (br, 1 H, NH). |
| 68 | 3-Cl, 2-(OEt) | H | Me | 1.41 (t, 3 H, J = 6.7 Hz), 3.9 (s, 3 H), 4.21 (q, 2 H, J = 6.9 Hz), 7.54-7.99 (m, 9 H), 8.67 (s, 1 H), 12.43 (br, 1 H, NH), 11.12 (br, 1 H, NH) |
| 69 | 3-Cl, 2-(OEt) | H | Et | 1.28 (t, 3 H, J = 7.2 Hz), 1.55 (t, 3 H, J = 6.9 Hz), 3.83 (q, 2 H, J = 7.1 Hz), 4.20 (q, 2 H, J = 7.1 Hz), 7.04 (d, 1 H, J = 8.6 Hz), 7.26 (s, 1 H), 7.39-7.82 (m, 8 H), 8.17 (s, 1 H). |
| 70 | 3-Cl, 2-(OPr) | H | H | 1.04 (t, 3 H, J = 7.3 Hz), 1.75-1.86 (m, 2 H), 4.12 (t, 2 H, J = 6.3 Hz), 6.79-7.7 (m, 7 H), 8.0 (d, 2 H, J = 7.8 Hz), 8.67 (s, 1 H). |
| 71 | 3-Br, 4-(OMe) | H | H | 3.94 (s, 3 H), 6.99-8.68 (m, 10 H) |
| 72 | 3-Br, 4-(OMe) | H | Me | 3.25 (s, 3 H), 3.98 (s, 3 H), 7.01 (m, 10 H). |
| 73 | 3-Br, 4-(OMe) | H | Et | 1.29 (t, 3 H, J = 7.2 Hz), 3.82 (q, 2 H, J = 7.2 Hz), 3.98 (s, 3 H), 7.01-8.17 (m, 10 H). |
| 74 | 3-Br, 4-(OMe) | H | Pr | 0.96 (t, 3 H, J = 7.4 Hz), 1.62-1.77 (m, 2 H), 3.72 (t, 2 H, J = 7.3 Hz), 7.00-8.16 (m, 10 H). |
| 75 | 3-Br, 4-(OMe) | H | CH$_2$CH=CHCH$_3$ | 3.98 (s, 3 H), 4.34-5.94 (m, 5 H), 7.01-8.18 (m, 10 H). |
| 76 | 3-Br, 4-(OMe) | H | CH$_2$C≡CH | 2.29 (t, 1 H, J = 2.5 Hz), 3.98 (s, 3 H), 4.51 (d, 2 H, J = 2.4 Hz), 7.01-8.17 (m, 10 H). |
| 77 | 3-Br, 4-(OEt) | H | H | 1.52 (t, 3 H, J = 7.1 Hz), 4.19 (q, 2 H, J = 7.1 Hz), 7.06 (d, 1 H, J = 8.6 Hz), 7.36-7.88 (m, 8 H), 8.26 (s, 1 H). |

TABLE 1g

| Comp. No. | Xn | Yn | R | ¹H NMR(CDCl₃) |
|---|---|---|---|---|
| 78 | 3-Br, 4-(OEt) | H | Me | 1.53 (t, 3 H, J = 7.2), 3.25 (s, 3 H), 4.19 (q, 2 H, J = 7.0), 7.0 (d, 1 H, J = 8.4), 7.39-7.55 (m, 4 H), 7.78 (d, 2 H, J = 7.8), 7.92 (d, 2 H, J = 2.1), 8.17 (s, 1 H). |
| 79 | 3-Br, 4-(OEt) | H | Et | 1.28 (t, 3 H, J = 7.2 Hz), 1.53 (t, 3 H, J = 7.1 Hz), 3.82 (q, 2 H, J = 7.2 Hz), 4.18 (q, 2 H, J = 6.9 Hz), 7.00 (d, 1 H, J = 8.7 Hz), 7.39 (t, 1 H, J = 7.4 Hz), 7.49-7.55 (m, 3 H), 7.78 (d, 2 H, J = 7.8 Hz), 7.89 (d, 2 H, J = 16.8 Hz), 8.16 (s, 1 H). |
| 80 | 3-Br, 4-(OEt) | H | –CH₂CH=CH₂ | 1.52 (t, 3 H, J = 7.1 Hz), 4.18 (q, 2 H, J = 6.8 Hz), 4.35 (d, 2 H, J = 5.6 Hz), 6.99 (d, 1 H, J = 8.6 Hz), 7.39-7.56 (m, 5 H), 7.78 (d, 2 H, J = 8.2 Hz), 7.99 (d, 2 H, J = 7.2 Hz), 8.17 (s, 1 H). |
| 81 | 3-Br, 4-(OEt) | H | –CH₂–C₆H₅ | 1.52 (t, 3 H, J = 7.3 Hz), 4.18 (q, 2 H, J = 7.2 Hz), 4.90 (s, 1 H), 6.99 (d, 1 H, J = 8.6 Hz), 7.31-7.56 (m, 10 H), 7.76 (d, 2 H, J = 7.4 Hz), 7.90 (d, 2 H, J = 9 Hz), 8.15 (s, 1 H). |
| 82 | 3-Br, 4-(OPr) | H | H | 0.98-1.08 (m, 3 H), 1.79-1.89 (m, 2 H), 4.09 (t, 2 H, J = 10.8 Hz), 7.27-8.02 (m, 9 H), 8.67 (s, 1 H) |
| 83 | 3-Br, 4-(OPr) | H | Me | 1.04 (t, 3 H, J = 7.3 Hz), 1.75-1.85 (m, 2 H), 3.32 (s, 3 H), 4.11 (t, 2 H, J = 6.5 Hz), 7.31-8.72 (m, 10 H). |
| 84 | 3-Br, 4-(OPr) | H | Et | 1.04 (t, 3 H, J = 7.4 Hz), 1.16 (t, 3 H, J = 7.1 Hz), 1.75-1.85 (m, 2 H), 3.67 (t, 2 H, J = 7.1 Hz), 4.12 (t, 2 H, J = 6.3 Hz), 7.31-8.73 (m, 10 H) |
| 85 | 3-Br, 4-(OPr) | H | Pr | 0.95 (t, 3 H, J = 7.4 Hz), 1.11 (t, 3 H, J = 7.3 Hz), 1.62-1.69 (m, 2 H), 1.85-1.95 (m, 2 H), 3.71 (t, 2 H, J = 4.2 Hz), 4.05 (t, 2 H, J = 6.4 Hz), 6.96-8.15 (m, 10 H). |
| 86 | 3-Br, 4-(OPr) | H | –CH₂CH=CH₂ | 1.03 (t, 3 H, J = 3.7 Hz), 1.78-1.81 (m, 2 H), 4.10 (t, 2 H, J = 4.9 Hz), 4.19 (d, 2 H, J = 23.9 Hz), 5.17 (d, 2 H, J = 9.0 Hz), 5.77-5.91 (m, 1 H), 7.27-9.45 (m, 10 H). |
| 87 | 3-Br, 4-(OPr) | H | –CH₂C≡CH | 0.84 (s, 1 H), 1.04 (t, 3 H, J = 7.1 Hz), 1.71-1.88 (m, 2 H), 4.10 (t, 2 H, J = 6.1 Hz), 4.41 (s, 2 H), 7.29-8.74 (m, 10 H). |
| 88 | 3-Br, 4-(OCH₂CH=CH₂) | H | H | 4.77 (d, 2 H, J = 3.9 Hz), 5.33 (d, 1 H J = 17.1 Hz), 5.51 (d, 1 H, J = 17.1 Hz) 6.06-6.15 (m, 1 H), 7.15-8.75 (m, 9 H), 8.70 (s, 1 H), 12.55 (br, 1 H). |
| 89 | 3-Br, 4-(OCH₂CH=CH₂) | H | Me | 3.25 (s, 3 H), 4.70 (d, 2 H, J = 5.1 Hz), 5.33 (d, 1 H, J = 1.42 Hz), 5.39 (d, 1 H, J = 7.4 Hz), 6.01-6.17 (m, 1 H), 6.99-8.16 (m, 10 H). |

TABLE 1h

| Comp. No. | Xn | Yn | R | ¹H NMR(CDCl₃) |
|---|---|---|---|---|
| 90 | 3-Br, 4-(OCH₂CH=CH₂) | H | Et | 1.25-1.32 (m, 3 H), 3.82 (q, 2 H, J = 7.2 Hz), 4.70 (d, 2 H, J = 4.9 Hz), 5.33 (d, 1 H, J = 3.1 Hz), 5.38 (d, 1 H, J = 1.4 Hz), 6.01-6.18 (m, 1 H), 6.98-8.16 (m, 10 H). |
| 91 | 3-Br, 4-(OCH₂CH=CH₂) | H | Pr | 0.85-0.99 (m, 3 H) 1.58-1.80 (m, 2 H), 3.71 (t, 2 H, J = 4.17 Hz), 4.69 (d, 2 H, J = 4.8 Hz), 5.38 (d, 1 H, J = 1.4 Hz), 5.57 (d, 1 H, J = 1.4 Hz), 6.01-6.18 (m, 1 H), 6.99-8.17 (m, 10 H). |
| 92 | 3-Br, 4-(OCH₂CH=CH₂) | H | –CH₂CH=CH₂ | 4.35 (d, 2 H, J = 5.9 Hz), 4.68 (d, 2 H, J = 1.1 Hz), 5.23-5.57 (m, 4 H), 5.77-6.20 (m, 2 H), 6.98-8.21 (m, 10 H). |
| 93 | 3-Br, 4-(OCH₂CH=CH₂) | H | –CH₂C≡CH | 2.28 (s, 1 H), 4.49 (s, 2 H), 4.69 (d, 1 H, J = 6.5 Hz), 5.38 (d, 1 H, J = 1.42 Hz), 5.57 (d, 1 H, J = 1.4 Hz), 6.01-6.18 (m, 1 H), 6.99-8.17 (m, 10 H). |

TABLE 1h-continued

| Comp. No. | Xn | Yn | R | ¹H NMR(CDCl₃) |
|---|---|---|---|---|
| 94 | 3-Br, 4-(O-CH₂-cyclopropyl) | H | H | 0.38-0.41 (m, 2 H), 0.59-0.66 (m, 2 H), 1.29-1.40 (m, 1 H), 4.02 (d, 2 H, J = 6.9 Hz), 7.10-8.69 (m, 10 H), 12.55 (br, 1 H). |
| 95 | 3-Br, 4-(O-CH₂-cyclopropyl) | H | Me | 0.43-0.48 (m, 2 H), 0.64-0.73 (m, 2 H), 1.26-1.40 (m, 1 H), 3.97 (d, 2 H, J = 6.7 Hz), 6.97-8.18 (m, 10 H) |
| 96 | 3-Br, 4-(O-CH₂-cyclopropyl) | H | Et | 0.41-0.48 (m, 2 H), 0.64-0.71 (m, 2 H), 1.25-1.40 (m, 4 H), 3.82 (q, 2 H, J = 7.2 Hz), 3.97 (d, 2 H, J = 6.77Hz), 6.97-8.17 (m, 10 H). |
| 97 | 3-Br, 4-(O-CH₂-cyclopropyl) | H | Pr | 0.41-0.46 (m, 2 H), 0.66-0.71 (m, 2 H), 1.26-1.56 (m, 1 H), 3.97 (d, 2 H, J = 6.5 Hz), 4.35 (d, 2 H, J = 4.48 Hz), 5.28 (m, 1 H), 5.32 (m, 1 H), 5.77-5.96 (m, 1 H), 6.97-8.18 (m, 10 H). |
| 98 | 3-Br, 4-(O-CH₂-cyclopropyl) | H | CH₂CH=CH-CH₃ | 0.43-0.44 (m, 2 H), 0.64-0.74 (m, 2 H), 0.96 (t, 3 H, J = 7.4 Hz), 1.29-1.43 (m, 1 H), 1.62-1.77 (m, 2 H), 3.72 (t, 2 H, J = 7.3 Hz), 3.97 (d, 2 H, J = 6.72 Hz), 6.97-8.17 (m, 10 H). |
| 99 | 3-Br, 4-(O-CH₂-cyclopropyl) | H | CH₂C≡CH | 0.43-0.48 (m, 2 H), 0.64-0.74 (m, 2 H), 1.25-1.40 (m, 1 H), 2.28 (s, 1 H), 3.97 (d, 2 H, J = 6.7 Hz), 4.51 (s, 1 H), 6.94-8.17 (m, 10 H). |
| 100 | 3-Br, 4-(O-CH₂C≡CH) | H | H | 3.69 (s, 1 H), 5.03 (s, 1 H), 7.14-8.69 (m, 10 H), 12.55 (br, 1 H). |
| 101 | 3-Br, 4-(O-CH₂C≡CH) | H | Me | 2.59 (s, 1 H), 3.25 (s, 3 H), 4.86 (s, 2 H), 7.17-8.17 (m, 10 H). |

TABLE 1i

| Comp. No. | Xn | Yn | R | ¹H NMR(CDCl₃) |
|---|---|---|---|---|
| 102 | 3-Br, 4-(O-CH₂C≡CH) | H | Et | 1.28 (t, 3 H, J = 7.1 Hz), 2.59 (s, 1 H), 3.82 (q, 2 H, J = 7.2 Hz), 4.85 (d, 2 H, J = 2.24 Hz)), 7.17-8.17 (m, 10 H). |
| 103 | 3-Br, 4-(O-CH₂C≡CH) | H | Pr | 0.96 (t, 3 H, J = 7.4 Hz), 1.66-1.77 (m, 2 H), 2.59 (s, 1 H), 3.72 (t, 2 H, J = 7.3 Hz), 4.85 (s, 2 H), 7.21-8.17 (m, 10 H) |
| 104 | 3-Br, 4-(O-CH₂C≡CH) | H | CH₂CH=CH₂ | 2.59 (s, 1 H), 4.35 (d, 2 H, J = 6.0 Hz), 4.85 (s, 2 H), 5.24-5.34 (m, 2 H), 5.82-5.91 (m, 1 H), 7.17-8.17 (m, 10 H) |
| 105 | 3-Br, 4-(O-CH₂C≡CH) | H | CH₂C≡CH | 2.28 (s, 1 H), 2.60 (s, 1 H), 4.51 (s, 2 H), 4.86 (s, 2 H), 7.18-8.17 (m, 10 H) |

TABLE 1i-continued

| Comp. No. | Xn | Yn | R | ¹H NMR(CDCl₃) |
|---|---|---|---|---|
| 106 | 3-Br, 4-OH | H | H | 3.36 (br, 1 H), 7.10-8.55 (m, 10 H) |
| 107 | 3-Br, 4-(OCH₂CF₃) | H | H | 5.01 (q, 2 H, J = 8.8 Hz), 7.40-7.70 (m, 6 H), 7.94 (s, 1 H), 8.04 (d, 2 H, J = 7.3 Hz), 8.71 (s, 2 H), 12.58 (br, 1 H, NH). |
| 108 | 3-Br, 4-(OCH₂CF₃) | H | Me | 3.25 (s, 3 H), 4.48 (q, 2 H, J = 8.0 Hz), 7.05 (d, 2 H, J = 8.5 Hz), 7.36-7.84 (m, 7 H), 7.95 (s, 1 H)), 8.17 (s, 1 H). |
| 109 | 3-Br, 4-(OCH₂CF₃) | H | Et | 1.28 (t, 3 H, J = 7.1 Hz), 3.82 (d, 2 H, J = 7.1 Hz), 4.48 (q, 2 H, J = 8.0 Hz), 7.06 (d, 2 H, J = 8.3 Hz), 7.35-784 (m, 7 H), 7.96 (s, 1 H), 8.17 (s, 1 H). |
| 110 | 3-Br, 4-(OCH₂CF₃) | H | Pr | 0.96 (t, 3 H, J = 7.2 Hz), 1.64-1.77 (m, 2 H), 3.72 (t, 2 H, J = 7.2 Hz), 4.48 (q, 2 H, J = 8.0 Hz), 7.07 (d, 2 H, J = 8.3 Hz), 7.37-7.85 (m, 7 H), 7.97 (s, 1 H), 8.17 (s, 1 H). |
| 111 | 3-I, 4-(OMe) | H | H | 3.96 (s, 3 H), 7.13-7.709 (m, 9 H), 8.16 (s, 1 H), 12.35 (br, 1 H) |
| 112 | 3-I, 4-(OMe) | H | Me | 3.52 (s, 3 H), 3.96 (s, 3 H), 6.94 (d, 2 H, J = 8.4 Hz), 7.31-7.58 (m, 4 H), 7.71-7.97 (m, 3 H), 8.16 (s, 2 H) |
| 113 | 3-I, 4-(OMe) | H | Et | 1.28 (t, 3 H, J = 7.2 Hz), 3.82 (d, 2 H, J = 7.2 Hz), 3.96 (s, 1 H), 6.95 (d, 2 H, J = 8.7 Hz), 7.4-7.80 (m, 6 H), 7.86 (s, 1 H), 8.16 (s, 2 H) |

TABLE 1j

| Comp. No. | Xn | Yn | R | ¹H NMR(CDCl₃) |
|---|---|---|---|---|
| 114 | 3-I, 4-(OMe) | H | Pr | 0.97 (t, 3 H, J = 7.4 Hz), 1.71-2.04 (m, 2 H), 3.72 (s, 3 H), 3.96 (s, 3 H), 7.28-7.87 (m, 8 H), 8.12 (s, 1 H) |
| 115 | 3-I, 4-(OEt) | H | H | 1.57 (t, 3 H, J = 6.9 Hz), 4.12 (q, 2 H, J = 6.9 Hz), 7.32-7.55 (m, 4 H), 7.68 (s, 1 H), 7.76-7.99 (m, 2 H), 8.07 (s, 1 H), 8.16 (s, 1 H), 11.62 (br, 1 H) |
| 116 | 3-I, 4-(OEt) | H | Me | 1.55 (t, 3 H, J = 6.9 Hz), 3.25 (s, 3 H), 4.13 (q, 2 H, J = 7.0 Hz), 7.38-7.56 (m, 3 H), 7.76-7.81 (m, 4 H), 8.05 (s, 2 H), 8.16 (s, 1 H) |
| 117 | 3-I, 4-(OEt) | H | Et | 1.58 (t, 3 H, J = 6.9 Hz), 3.84 (q, 2 H, J = 6.9 Hz), 4.13 (q, 2 H, J = 6.9 Hz), 7.40-7.81 (m, 6 H), 8.06 (s, 3 H), 8.16 (s, 1 H) |
| 118 | 3-I, 4-(OEt) | H | Pr | 0.96 (t, 3 H, J = 7.4 Hz), 1.56 t, 3 H, J = 7.0 Hz), 1.72 (q, 2 H, J = 7.4 Hz), 3.73 (t, 3 H, J = 7.4 Hz), 4.12 (q, 2 H, J = 7.0 Hz), 7.40-7.56 (m, 2 H), 7.76-7.80 (m, 4 H), 8.06 (s, 2 H), 8.16 (s, 1 H). |
| 119 | 3-I, 4-(OEt) | H | CH₂CH=CH₂ | 1.55 (t, 3 H, J = 7.0 Hz), 4.13 (q, 2 H, J = 7.0 Hz), 4.52 (s, 2 H), 7.39-7.56 (m, 3 H), 7.76-7.78 (m, 2 H), 7.79 (s, 1 H), 8.05 (s, 2 H), 8.16 (s, 1 H) |
| 120 | 3-I, 4-(OEt) | H | CH₂C≡CH | 1.55 (t, 3 H, J = 7.0 Hz), 4.12 (q, 2 H, J = 7.0 Hz), 4.36 (d, 2 H, J = 6.0 Hz), 5.25-5.35 (m, 2 H), 5.83-5.86 (m, 1 H), 7.40-7.56 (m, 3 H), 7.76-7.82 (m, 4 H), 8.05 (s, 2 H), 8.16 (s, 1 H) |
| 121 | 3-I, 4-(OEt) | H | Na | |
| 122 | 3-I, 4-(OPr) | H | H | 1.08 (t, 3 H, J = 7.3 Hz), 1.80-1.91 (m, 2 H), 4.01 (t, 2 H, J = 7.3 Hz), 7.19-8.02 (m, 9 H), 8.69 (s, 1 H), 12.56 (br, 1 H) |
| 123 | 3-I, 4-(OPr) | H | Me | 1.15 (t, 3 H, J = 7.4 Hz), 1.96-2.03 (m, 3 H), 3.25 (s, 3 H), 4.02 (t, 2 H, J = 7.4 Hz), 7.26-7.56 (m, 4 H), 7.76-7.81 (m, 3 H), 8.05 (s, 2 H), 8.16 (s, 1 H) |
| 124 | 3-I, 4-(OPr) | H | Et | 1.16 (t, 3 H, J = 6.9 Hz), 1.29 (t, 2 H, J = 5.0 Hz), 1.92-2.05 (m, 2 H), 3.82 (q, 2 H, J = 6.9 Hz), 4.09 (t, 2 H, J = 5.0 Hz), 7.26 (s, 1 H), 7.29-7.35 (m, 1 H), 7.41-7.53 (m, 2 H), 7.72-7.81 (m, 3 H), 8.05 (s, 1 H), 8.16 (s, 1 H) |
| 125 | 3-I, 4-(OPr) | H | Pr | 0.96 (t, 3 H, J = 7.5 Hz), 1.16 (t, 3 H, J = 7.4 Hz), 1.71-1.73 (m, 2 H), 1.96-2.02 (m, 2 H), 3.73 (t, 2 H, J = 7.5 Hz), 4.01 (t, 2 H, J = 7.5 Hz), 7.40-7.56 (m, 4 H), 7.76-7.80 (m, 3 H), 8.06 (s, 2 H), 8.16 (s, 1 H). |

TABLE 1k

| Comp. No. | Xn | Yn | R | $^1$H NMR(CDCl$_3$) |
|---|---|---|---|---|
| 126 | 3-I, 4-(OPr) | H | (propargyl) | 1.14 (t, 3 H, J = 7.4 Hz), 1.55 (t, 1 H, J = 6.8 Hz), 1.93-2.05 (m, 2 H), 4.01 (t, 3 H, J = 7.4 Hz), 4.36 (d, 2 H, J = 6.8 Hz), 7.26 (s, 1 H), 7.38-7.43 (m, 1 H), 7.50-7.56 (m, 2 H), 7.76-7.82 (m, 3 H), 8.06 (s, 2 H), 8.16 (s, 1 H) |
| 127 | 3-I, 4-(OPr) | H | Na | |
| 128 | 3-I, 4-(O-allyl) | H | H | 4.42 (d, 2 H, J = 5.7 Hz), 5.09-5.24 (m, 2 H), 5.82-5.88 (m, 1 H), 7.37-7.55 (m, 3 H), 7.65 (s, 1 H), 7.78-7.94 (m, 4 H), 8.18 (s, 1 H), 12.60 (br, 1 H), 7.15-8.75 (m, 9 H), 12.60 (br, 1 H). |
| 129 | 3-I, 4-(O-allyl) | H | Me | 3.26 (s, 3 H), 4.59 (d, 2 H, J = 5.7 Hz), 5.35-5.38 (m, 1 H), 5.53-5.59 (m, 1 H), 6.12-6.34 (m, 1 H), 7.41-7.43 (m, 2 H), 7.53-7.56 (m, 2 H), 7.79 (m, 3 H), 8.06 (s, 1 H), 8.16 (s, 1 H) |
| 130 | 3-I, 4-(O-allyl) | H | Et | 1.29 (t, 3 H, J = 7.2 Hz), 3.83 (q, 2 H, J = 7.2 Hz), 4.59 (d, 2 H, J = 5.7 Hz), 5.35-5.59 (m, 2 H), 6.24-6.26 (m, 1 H), 7.38-7.43 (m, 2 H), 7.51-7.56 (m, 2 H), 7.76-7.85 (m, 3 H), 8.06-8.16 (s, 3 H) |
| 131 | 3-I, 4-(O-allyl) | H | Pr | 0.97 (t, 3 H, J = 7.4 Hz), 1.75 (m, 2 H), 3.73 (t, 2 H, J = 7.4 Hz), 4.59 (d, 2 H, J = 5.7 Hz), 5.37 (m, 1 H), 5.53-5.59 (m, 1 H), 6.20-6.30 (m, 1 H), 7.38-7.43 (m, 1 H), 7.51-7.56 (m, 2 H), 7.76-7.85 (m, 4 H), 8.06-8.07 (m, 2 H), 8.16 (s, 1 H) |
| 132 | 3-I, 4-(O-allyl) | H | (allyl) | 4.36 (d, 2 H, J = 5.9 Hz), 4.59 (d, 2 H, J = 5.8 Hz), 5.02-5.25 (m, 4 H), 5.40-5.78 (m, 2 H), 7.52-7.93 (m, 9 H), 8.18 (s, 1 H). |
| 133 | 3-I, 4-(O-allyl) | H | (propargyl) | 2.38 (t, 1 H, J = 2.4 Hz), 4.52 (d, 2 H, J = 2.4 Hz), 4.59 (d, 2 H, J = 5.7 Hz), 5.37-5.59 (m, 2 H), 6.02-6.23 (m, 1 H), 7.41-7.56 (m, 4 H), 7.76-7.86 (m, 3 H), 8.00-8.17 (m, 3 H). |
| 134 | 3-I, 4-(O-allyl) | H | Na | |
| 135 | 3-Me, 4-(OMe) | H | H | 2.23 (s, 3 H), 3.86 (s, 3 H), 6.33 (s, 3 H), 7.10 (d, 1 H, J = 8.1 Hz), 7.36-7.60 (m, 5 H), 7.93 (d, 2 H, J = 7.7 Hz), 9.06 (s, 1 H), 10.41 (br, 1 H, NH) |
| 136 | 3-Pr$^i$, 4-(OMe) | H | H | 1.81 (d, 6 H, J = 6.8 Hz), 2.70 (t, 1 H), 3.86 (s, 3 H), 6.22 (s, 3 H), 7.10-7.93 (m, 8 H), 9.06 (s, 1 H), 10.20 (br, 1 H, NH) |
| 137 | 3-Pr$^i$, 4-(OEt) | H | H | 1.29 (d, 6 H, J = 6.8 Hz), 1.47 (t, 3 H, J = 6.9 Hz), 3.39 (m, 1 H), 4.12 (q, 2 H, J = 6.9 Hz), 6.95 (d, 1 H, J = 8.6 Hz), 7.26-7.48 (m, 5 H), 7.80 (d, 2 H, J = 7.4 Hz), 7.96 (s, 1 H), 8.17 (s, 1 H), 10.0 (br, 1 H, NH) |

TABLE 1l

| Comp. No. | Xn | Yn | R | $^1$H NMR(CDCl$_3$) |
|---|---|---|---|---|
| 138 | 3-Pr$^1$, 4-(OEt) | H | Me | 1.29 (d, 6 H, J = 6.8 Hz), 1.47 (t, 3 H, J = 6.9 Hz), 3.25 (s, 3 H), 3.39 (m, 1 H), 4.12 (q, 2 H, J = 6.9 Hz), 6.95 (d, 1 H, J = 8.6 Hz), 7.26-7.48 (m, 5 H), 7.80 (d, 2 H, J = 7.4 Hz), 7.96 (s, 1 H), 8.17 (s, 1 H). |
| 139 | 3-Pr$^i$, 4-(OEt) | H | Et | 1.28 (d, 9 H, J = 5.6 Hz), 1.51 (q, 3 H, J = 5.3 Hz), 3.39 (m, 1 H), 3.81 (d, 2 H, j = 7.4 Hz), 4.13 (t, 3 H, J = 3.6 Hz), 6.95 (d, 1 H, J = 8.6 Hz), 7.41 (m, 4 H), 7.80 (d, 2 H, J = 7.2 Hz), 7.95 (s, 1 H), 8.16 (s, 1 H). |
| 140 | 3-Pr$^i$, 4-(OEt) | H | Benzyl | 1.28 (d, 6 H, J = 6.8 Hz), 1.44-1.56 (m, 3 H), 3.39 (t, 1 H, J = 6.9 Hz), 4.11 (q, 2 H, J = 6.9 Hz), 4.89 (s, 2 H), 6.9 (d, 1 H, J = 8.6 Hz), 7.31-7.56 (m, |

TABLE 1l-continued

| Comp. No. | Xn | Yn | R | $^1$H NMR(CDCl$_3$) |
|---|---|---|---|---|
|  |  |  |  | 10 H), 7.79 (d, 2 H, J = 7.6 Hz), 7.95 (s, 1 H), 8.15 (s, 1 H). |
| 141 | 3-Pr$^i$, 4-(OPr) | H | H | 1.04 (t, 3 H, J = 7.4 Hz), 1.23 (d, 6 H, J = 6.8 Hz), 1.62-1.84 (m, 2 H), 3.91-4.09 (m, 2 H), 7.42-8.04 (m, 10 H), 8.76 (s, 1 H). |
| 142 | 3-Bu$^t$, 4-(OPr) | H | H | 1.08 (t, 3 H, J = 7.5 Hz), 1.41 (s, 9 H), 1.85 (m, 2 H), 4.06 (t, 2 H J = 5.7 Hz), 7.13-8.03 (m, 9 H), 8.67 (s, 1 H), 12.52 (br, 1 H, NH). |
| 143 | 3-( ), 4-(OMe) | H | H | 1.58-1.91 (m, 8 H), 3.83 (s, 3 H), 4.85 (m, 1 H), 7.14-8.03 (m, 9 H), 8.68 (s, 1 H), 12.51 (br, 1 H, NH) |
| 144 | 3-( ), 4-(OMe) | H | Me | 1.56-1.99 (m, 8 H), 3.25 (s, 3 H), 3.92 (s, 3 H), 6.97-8.18 (m, 10 H) |
| 145 | 3,5-di(Br), 4-(OMe) | H | H | 3.96 (s, 3 H), 7.13-7.80 (m, 8 H), 8.16 (s, 1 H), 11.35 (br, 1 H) |
| 146 | 3,5-di(Br), 4-(OMe) | H | Me | 3.25 (s, 3 H), 3.96 (s, 3 H), 7.25-7.82 (m, 8 H), 8.17 (s, 1 H) |
| 147 | 3,5-di(Br), 4-(OMe) | H | Et | 1.25 (t, 3 H, J = 7.3 Hz), 3.83 (q, 2 H, J = 7.3 Hz), 3.97 (s, 3 H), 7.23-7.97 (m, 8 H), 8.17 (s, 1 H) |
| 148 | 3,5-di(Br), 4-(OMe) | H | Pr | 0.97 (t, 3 H, J = 10.8 Hz), 1.71-2.04 (m, 2 H), 3.07 (t, 22, J = 10.8 Hz), 3.95 (s, 3 H), 7.27-7.95 (m, 8 H), 8.18 (s, 1 H) |
| 149 | 3,5-di(Br), 4-(OMe) | H |  | 3.96 (s, 3 H), 4.36 (d, 2 H, J = 6.0 Hz), 5.25-5.35 (m, 2 H), 5.83-5.92 (m, 1 H), 7.39-7.44 (m, 1 H), 7.51-7.56 (m, 2 H), 7.76-7.83 (m, 5 H), 8.18 (s, 1 H) |

TABLE 1m

| Comp. No. | Xn | Yn | R | $^1$H NMR(CDCl$_3$) |
|---|---|---|---|---|
| 150 | 3,5-di(Br), 4-(OMe) | H |  | 1.56 (t, 3 H, J = 2.4 Hz), 3.97 (s, 3 H), 4.52 (d, 2 H, J = 2.4 Hz), 7.26-7.87 (m, 8 H), 8.12 (s, 1 H) |
| 151 | 3,5-di(Br), 4-(OEt) | H | H | 1.53 (t, 3 H, J = 6.9 Hz), 4.16 (q, 2 H, J = 6.9 Hz), 7.31-7.82 (m, 8 H), 8.25 (s, 1 H), 11.6 (br, 1 H) |
| 152 | 3,5-di(Br), 4-(OEt) | H | Me | 1.54 (t, 3 H, J = 3.6 Hz), 3.27 (s, 3 H), 4.17 (q, 2 H, J = 3.6 Hz), 7.26-7.81 (m, 8 H), 8.18 (s, 1 H). |
| 153 | 3,5-di(Br), 4-(OEt) | H | Et | 1.29 (t, 3 H, J = 10.7 Hz), 1.54 (t, 3 H, J = 12 Hz), 3.83 (q, 2 H, J = 10.7 Hz), 4.17 (q, 3 H, J = 12 Hz), 7.28-7.82 (m, 8 H), 8.17 (s, 1 H). |
| 154 | 3,5-di(Br), 4-(OEt) | H | Pr | 0.97 (t, 3 H, J = 7.4 Hz), 1.56 (t, 3 H, J = 6.9 Hz), 1.71-1.78 (m, 2 H), 3.74 (t, 2 H, J = 7.4 Hz), 4.17 (q, 2 H, J = 6.9 Hz), 7.41-7.81 (m, 9 H), 8.18 (s, 1 H). |
| 155 | 3,5-di(Br), 4-(OEt) | H | 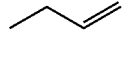 | 1.56 (t, 3 H, J = 6.9 Hz), 4.17 (q, 2 H, J = 6.9 Hz), 4.36 (d, 2 H, J = 5.8 Hz), 5.19-5.37 (m, 2 H), 5.69-5.94 (m, 1 H), 7.28-7.92 (m, 8 H), 8.18 (s, 1 H). |
| 156 | 3,5-di(Br), 4-(OEt) | H | 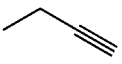 | 1.55 (t, 3 H, J = 6.8 Hz), 2.30 (t, 1 H, J = 7.3 Hz), 4.18 (q, 2 H, J = 6.8 Hz), 4.52 (d, 2 H, J = 7.3 Hz), 7.42-7.88 (m, 8 H), 8.18 (s, 1 H). |
| 157 | 3,5-di(Br), 4-(OPr) | H | H | 1.50-1.57 (m, 6 H), 4.12-4.31 (m, 4 H), 7.41-7.81 (m, 8 H), 8.19 (s, 1 H). |
| 158 | 3,5-di(Br), 4-(OPr) | H | Me | 1.36 (t, 3 H, J = 6.6 Hz), 1.86-2.04 (m, 2 H), 3.26 (s, 3 H) 4.05 (t, 2 H, J = 6.5 Hz) 7.40-7.84 (m, 8 H), 8.17 (s, 1 H) |
| 159 | 3,5-di(Br), 4-(OPr) | H | Et | 1.14 (t, 3 H, J = 10.8 Hz), 1.29 (t, 3 H, J = 10.0 Hz), 1.93-2.0 (m, 2 H), 3.83 (q, 2 H, J = 10.8 Hz), 4.05 (t, 2 H, J = 10.0 Hz), 7.41-8.17 (m, 8 H), 9.56 (s, 1 H) |
| 160 | 3,5-di(Br), 4-(OPr) | H | Pr | 0.97 (t, 3 H, J = 4.7 Hz), 1.13 (t, 2 H, J = 3.4 Hz), 1.71-197 (m, 4 H), 3.52 (t, 2 H, J = 4.7 Hz), 4.05 (t, 2 H, J = 3.4 Hz), 7.42-7.82 (m, 8 H), 8.18 (s, 1 H) |

TABLE 1m-continued

| Comp. No. | Xn | Yn | R | $^1$H NMR(CDCl$_3$) |
|---|---|---|---|---|
| 161 | 3,5-di(Br), 4-(OPr) | H | (allyl/propenyl group) | 1.13 (t, 3 H, J = 7.5 Hz), 1.89-1.98 (m, 2 H), 4.05 (t, 3 H, J = 7.5 Hz), 4.36 (d, 2 H, J = 6.0 Hz), 5.25-5.35 (m, 2 H), 5.81-5.92 (m, 1 H), 7.38-7.56 (m, 3 H), 7.70-7.84 (m, 5 H), 8.17 (s, 1 H) |

TABLE 1n

| Comp. No. | Xn | Yn | R | $^1$H NMR(CDCl$_3$) |
|---|---|---|---|---|
| 162 | 3,5-di(Br), 4-(OPr) | H | (propargyl group) | 1.14 (t, 3 H, J = 7.5 Hz), 1.85-2.1 (m, 2 H), 2.29 (t, 1 H, J = 2.1 Hz), 4.05 (t, 2 H, J = 7.5 Hz), 4.51 (d, 2 H, J = 2.1 Hz), 7.39-7.56 (m, 3 H), 7.76-7.87 (m, 5 H), 8.17 (s, 1 H) |
| 163 | 3,5-di(Br), 4-(OPr) | H | Na | |
| 164 | 3,5-di(Br), 4-(OCH$_2$CH=CH$_2$) | H | H | 4.59 (d, 2 H, J = 5.7 Hz), 5.35-5.58 (m, 2 H), 6.24-6.28 (m, 1 H), 7.19-7.25 (m, 1 H), 7.41-7.56 (m, 4 H), 7.76-7.78 (m, 3 H), 8.05 (s, 1 H) 8.15 (s, 1 H), 12.06 (br, 1 H). |
| 165 | 3,5-di(Br), 4-(OCH$_2$CH=CH$_2$) | H | Me | 3.21 (s, 3 H), 4.42 (d, 2 H, J = 5.6 Hz), 5.09-5.30 (m, 2 H), 5.77-5.97 (m, 1 H), 7.35-7.93 (m, 8 H), 8.18 (s, 1 H). |
| 166 | 3,5-di(Br), 4-(OCH$_2$CH=CH$_2$) | H | Et | 1.25 (t, 3 H, J = 7.2 Hz), 3.77 (q, 2 H, J = 7.2 Hz), 4.42 (d, 2 H, J = 5.7 Hz), 5.09-5.24 (m, 2 H), 5.82-5.88 (m, 1 H), 7.37-7.55 (m, 3 H), 7.65 (s, 1 H), 7.78-7.94 (m, 4 H), 8.18 (s, 1 H). |
| 167 | 3,5-di(Br), 4-(OCH$_2$CH=CH$_2$) | H | Pr | 0.97 (t, 3 H, J = 4.7 Hz), 1.13 (t, 2 H, J = 3.4 Hz), 1.71-1.97 (m, 2 H), 4.42 (d, 2 H, J = 5.7 Hz), 5.09-5.24 (m, 2 H), 5.82-5.88 (m, 1 H), 7.37-7.55 (m, 3 H), 7.65 (s, 1 H), 7.78-7.94 (m, 4 H), 8.18 (s, 1 H). |
| 168 | 3,5-di(Br), 4-(OCH$_2$CH=CH$_2$) | H | (allyl group) | 4.36 (d, 2 H, J = 5.9 Hz), 4.59 (d, 2 H, J = 5.8 Hz), 5.02-5.25 (m, 4 H), 5.40-5.78 (m, 2 H), 7.52-7.93 (m, 8 H), 8.18 (s, 1 H). |
| 169 | 3,5-di(Br), 4-(OCH$_2$CH=CH$_2$) | H | (propargyl group) | 2.38 (t, 1 H, J = 2.4 Hz), 4.52 (d, 2 H, J = 2.4 Hz), 4.59 (d, 2 H, J = 5.7 Hz), 5.37-5.59 (m, 2 H), 6.02-6.23 (m, 1 H), 7.41-7.56 (m, 4 H), 7.76-7.86 (m, 3 H), 8.00-8.17 (m, 2 H). |
| 170 | 3,5-di(Br), 4-(OCH$_2$CH=CH$_2$) | H | Na | |
| 171 | 3,5-di(Br), 4-(OCH$_2$CH=CH$_2$) | H | H | 0.44-0.47 (m, 2 H), 0.65-0.71 (m, 2 H), 1.25-1.46 (m, 1 H), 3.94 (d, 2 H, J = 7.2 Hz), 7.34-7.55 (m, 3 H), 7.34-7.55 (m, 5 H), 7.70-7.80 (m, 5 H), 8.17 (s, 1 H), 11.79-11.92 (br, 1 H) |
| 172 | 3,5-di(Br), 4-(OCH$_2$CH=CH$_2$) | H | Me | 0.44-0.47 (m, 2 H), 0.66-0.70 (m, 2 H), 1.45-1.51 (m, 1 H), 3.26 (s, 3 H), 3.95 (d, 2 H, J = 7.2 Hz), 7.38-7.56 (m, 3 H), 7.38-7.56 (m, 3 H), 7.76-7.83 (m, 5 H), 8.17 (s, 1 H) |
| 173 | 3,5-di(Br), 4-(OCH$_2$-cyclopropyl) | H | Et | 0.44-0.47 (m, 2 H), 0.66-0.72 (m, 2 H), 1.30 (t, 3 H, J = 7.2 Hz), 1.45-1.55 (m, 1 H), 3.83 (q, 2 H, J = 7.2 Hz), 3.95 (d, 2 H, J = 7.2 Hz), 7.38-7.56 (m, 3 H), 7.74-7.82 (m, 5 H), 8.17 (s, 1 H) |

TABLE 1o

| Comp. No. | Xn | Yn | R | $^1$H NMR(CDCl$_3$) |
|---|---|---|---|---|
| 174 | 3,5-di(Br), 4-(O-cyclopropylmethyl) | H | Pr | 0.44-0.47 (m, 2 H), 0.66-0.69 (m, 2 H), 0.97 (t, 3 H, J = 7.4 Hz), 1.42-1.45 (m, 1 H), 1.55-1.76 (m, 2 H), 3.73 (t, 2 H, J = 7.2 Hz), 3.95 (d, 2 H, J = 7.4 Hz), 7.38-7.43 (m, 3 H), 7.76-7.82 (m, 5 H), 8.17 (s, 1 H) |
| 175 | 3,5-di(Br), 4-(O-cyclopropylmethyl) | H | allyl | 0.44-0.47 (m, 2 H), 0.66-0.69 (m, 2 H), 1.40-1.43 (m, 1 H), 3.95 (d, 2 H, J = 7.2 Hz), 4.36 (d, 2 H, J = 6.0 Hz), 5.29 (t, 2 H, J = 14.9 Hz), 5.86 (m, 1 H), 7.41-7.43 (m, 1 H), 7.53-7.56 (m, 2 H), 7.74-7.84 (m, 5 H), 8.17 (s, 1 H) |
| 176 | 3,5-di(Br), 4-(O-cyclopropylmethyl) | H | propargyl | 0.44-0.47 (m, 2 H), 0.66-0.72 (m, 2 H), 1.42-1.46 (m, 1 H), 2.29 (t, 1 H, J = 4.4 Hz), 3.95 (d, 2 H, J = 7.2 Hz), 4.51 (d, 2 H, J = 4.4 Hz), 7.39-7.44 (m, 1 H), 7.51-7.56 (m, 2 H), 7.76-7.80 (m, 4 H), 7.88 (s, 1 H), 8.17 (s, 1 H) |
| 177 | 3,5-di(Br), 4-(O-cyclopropylmethyl) | H | Na | |
| 178 | 3,5-di(Br), 4-(OCHF$_2$) | H | H | 6.48-6.97 (m, 1 H), 7.42-7.57 (m, 3 H), 7.66 (s, 1 H), 7.78-7.81 (m, 2 H), 7.90 (s, 2 H), 8.23 (s, 1 H). |
| 179 | 3,5-di(Br), 4-(OCHF$_2$) | H | Me | 3.26 (s, 3 H), 6.33-7.06 (m, 1 H), 7.42-7.89 (m, 8 H) 8.20 (s, 1 H). |
| 180 | 3,5-di(Br), 4-(OCHF$_2$) | H | Et | 0.88 (t, 3 H, J = 7.1 Hz), 3.83 (q, 2 H, J = 7.1 Hz), 6.44-7.26 (s, 1 H), 7.40-7.57 (m, 3 H), 7.76-7.89 (m, 5 H), 8.18 (s, 1 H). |
| 181 | 3,5-di(Br), 4-(OCHF$_2$) | H | Pr | 0.97 (t, 3 H, J = 7.4 Hz), 1.72-1.85 (m, 2 H), 3.73 (t, 2 H, J = 7.4 Hz), 6.44-6.93 (m, 1 H), 7.40-7.57 (m, 3 H), 7.76-7.79 (m, 3 H), 7.90 (s, 2 H), 8.19 (s, 1 H). |
| 182 | 3,5-di(Br), 4-(OCHF$_2$) | H | allyl | 4.37 (d, 2 H, J = 4.4 Hz), 5.25-5.27 (m, 2 H), 5.81-5.94 (m, 1 H), 6.32-6.69 (m, 1 H), 7.42-7.90 (m, 8 H), 8.19 (s, 1 H). |
| 183 | 3,5-di(Br), 4-(OCHF$_2$) | H | propargyl | 1.52 (t, 1 H, J = 2.4 Hz), 4.52 (d, 2 H, J = 2.4 Hz), 6.32-7.06 (m, 1 H), 7.43-7.89 (m, 8 H), 8.19 (s, 1 H). |
| 184 | 3,5-di(Pr$^i$), 4-(OMe) | H | H | 1.243 (d, 12 H, J = 6.8 Hz), 3.335-3.4025 (m, 2 H), 3.7498 (s, 3 H), 7.3467-8.0155 (m, 9 H) |
| 185 | 3,5-di(Pr$^i$), 4-(OEt) | H | H | 1.2375 (d, 12 H, J = 7.0 Hz), 1.415 (t, 3 H, J = 7.0 Hz), 3.328 (m, 2 H), 3.842 (q, 2 H, J = 7.0 Hz), 7.300-8.0035 (m, 8 H), 8.648 (s, 1 H), 10.412 (Br, 1 H) |

TABLE 1p

| Comp. No. | Xn | Yn | R | $^1$H NMR(CDCl$_3$) |
|---|---|---|---|---|
| 186 | 3,5-di(Pr$^i$), 4-(OEt) | H | Me | 1.302 (d, 12 H, J = 7.0 Hz), 1.490 (t, 3 H, J = 7.0 Hz), 3.349 (s, 3 H), 3.395 (m, 2 H), 3.8745 (q, 2 H, J = 7.0 Hz), 7.361-7.844 (m, 7 H), 7.973 (s, 1 H), 8.182 (s, 1 H) |
| 187 | 3,5-di(Pr$^i$), 4-(OEt) | H | Et | 1.303 (d, 12 H, J = 7.0 Hz), 1.271 (t, 3 H, J = 7.0 Hz), 1.487 (t, 3 H, J = 7.0 Hz), 3.326-3.760 (m, 2 H), 3.843 (q, 4 H, J = 7.0 Hz), 7.365-7.563 (m, 7H), 7.797 (s, 1 H), 8.178 (s, 1 H) |
| 188 | 3,5-di(Pr$^i$), 4-(OEt) | H | Pr | 0.948 (d, 3 H, J = 7.0 Hz), 1.308 (d, 12 H, J = 7.0 Hz), 1.492 (t, 3 H, J = 7.0 Hz), 3.391-3.469 (m, 2 H), 3,716 (t, 2 H, J = 4.2 Hz), 3.875 (q, 2 H, J = 7.0 Hz) 7.340-7.807 (m, 6 H), 7.958 (s, 1 H), 8.181 (s, 1 H) |
| 189 | 3,5-di(Pr$^i$), 4-(OEt) | H | propargyl | 1.302 (d, 12 H, J = 7.0 Hz), 1.491 (t, 3 H, J = 7.0 Hz), 2.050 (s, 1 H), 3.293-3.466 (m, 2 H), 3.874 (q, 2 H, J = 7.0 Hz), 4.499 (s, 2 H), 7.360-7.838 (m, 7 H), 8.011 (s, 1 H), 8.186 (s, 1 H) |

TABLE 1p-continued

| Comp. No. | Xn | Yn | R | $^1$H NMR(CDCl$_3$) |
|---|---|---|---|---|
| 190 | 3,5-di(Pr$^i$), 4-(OPr) | H | H | 1.07 (t, 3 H, J = 7.3 Hz), 1.24 (d, 12 H, J = 7.0 Hz), 1.80-1.87 (m, 2 H), 3.67-3.96 (m, 2 H), 7.34-8.68 (m, 9 H), 8.68 (s, 1 H), 12.49 (br, 1 H, NH) |
| 191 | 3,5-di(Pr$^i$), 4-(OPr) |  | H | 1.09 (t, 3 H, J = 7.2 Hz), 1.26 (d, 12 H, J = 7.0 Hz), 1.82-1.88 (m, 2 H), 3.65-3.95 (m, 2 H), 7.40-8.80 (m, 8 H), 8.70 (s, 1 H), 12.90 (br, 1 H, NH) |
| 192 | 3,5-di(Bu$^t$), 4-OH | H | H | 1.27 (s, 18 H), 6.92-7.02 (m, 1 H), 7.17-7.28 (m, 2 H), 7.39 (t, 2 H, J = 7.8 Hz), 7.50 (s, 1 H), 7.82 (d, 2 H, J = 8.4 Hz), 8.48 (s, 1 H), 12.31 (br, 1 H, NH) |
| 193 | 3,5-di(Bu$^t$), 4-(OPr) | H | H | 1.07 (t, 3 H, J = 7.3 Hz), 1.24 (d, 12 H, J = 7.0 Hz), 1.80-1.87 (m, 2 H), 3.67-3.96 (m, 2 H), 7.34-8.68 (m, 9 H), 8.68 (s, 1 H), 1249 (br, 1 H, NH) |
| 194 | 3,5-di(Bu$^t$), 4-(OPr) | H | Et | 1.09 (t, 3 H, J = 7.3 Hz), 1.24 (d, 12 H, J = 7.0 Hz), 3.68-3.80 (m, 2 H), 3.843 (q, 4 H, J = 7.0 Hz), 7.365-7.563 (m, 7 H), 7.797 (s, 1 H), 8.178 (s, 1 H) |
| 195 | 3,5-di(Bu$^t$), 4-(OCH$_2$C(O)OEt) | H | H | 1.26 (t, 3 H, J = 7.2 Hz), 1.43 (s, 18 H), 4.25 (q, 2 H, J = 7.0 Hz), 4.44 (s, 2 H), 7.42 (t, 2 H, J = 7.2 Hz), 7.46-7.66 (m, 5 H), 8.01 (d, 2 H, J = 8.4 Hz), 8.68 (s, 1 H), 12.29 (br, 1 H, NH). |

EXAMPLE 7

Preparation Forms Comprising the Compound of the Formula 1 as an Active Ingredient The compound of the formula 1 can be prepared into various preparation forms, depending on the purpose. Hereunder are given a few examples of the preparation forms comprising the compound of the formula 1 as an active ingredient, which do not limit the scope of the present invention.

Preparation Form 1: Tablet (Direct Compression)

5.0 mg of the active ingredient was sieved, mixed with 14.1 mg of lactose, 0.8 mg of Crospovidone USNF and 0.1 mg of magnesium stearate. The mixture was compressed into a tablet.

Preparation Form 2: Tablet (Wet Granulation)

5.0 mg of the active ingredient was sieved and mixed with 16.0 mg of lactose and 4.0 mg of starch. 0.3 mg of Polysorbate 80 dissolved in pure water was added and the mixture was granulated. After drying, the granule was sieved and mixed with 2.7 mg of colloidal silicon dioxide and 2.0 mg of magnesium stearate. The granule was compressed into a tablet.

Preparation Form 3: Powder and Capsule 5.0 mg of the active ingredient was sieved and mixed with 14.8 mg of lactose, 10.0 mg of polyvinylpyrrolidone and 0.2 mg of magnesium stearate. The mixture was filled in a No. 5 gelatin capsule using an adequate apparatus.

EXAMPLE 8

CDC25B Enzyme Assay

Catalytic domain of CDC25B (aa 378-566) was expressed and produced in *E. coli* into a GST fusion protein, which was used as zymogen. Enzyme assay was carried out on a 96-well plate, with the final reaction volume per well adjusted to 200 μL. 170 μL of a buffer solution (30 mM Tris buffer, pH 8.5, 75 mM NaCl, 0.67 mM EDTA, 1 mM DTT), 20 μL (0.2 μg) of CDC25B enzyme and 10 μL of the test compound dissolved in DMSO were added, so that the final concentration became 1 μg/mL CDC25B and 20 μm FDP. Measurement was made after culturing at room temperature for 1 hour. FDP and DTT were added to the buffer solution just before assay, so that a fresh status could be maintained. After 1 hour of culturing, fluorescence resultant from the enzymatic reaction was measured at 485 nm (excitation) and 538 nm (emission).

The test compound was treated to a final concentration of 10 μm to screen out one showing superior inhibitory activity, from which the IC$_{50}$ value was measured. The screened compound was treated to a final concentration of 1, 2, 5 and 10 μm to obtain the % inhibition value. If the inhibitory effect was low (less than 50% at 20 μm), the concentration of the compound was increased to 20 μm and the % inhibition value and the IC$_{50}$ value were obtained.

Of the compounds given in Table 1a-1p, CDC25B % inhibition values and IC$_{50}$ values of those having superior activity are given in Table 2 below.

TABLE 2

| Compound No. | IC$_{50}$ (μM) |
|---|---|
| 2 | 11.41 |
| 3 | 9.45 |
| 5 | 8.96 |
| 14 | 1.03 |
| 15 | 8.28 |
| 16 | 0.23 |
| 25 | 1.86 |
| 30 | 5.74 |
| 35 | 1.52 |
| 41 | 0.54 |
| 52 | 2.83 |
| 58 | 5.79 |
| 62 | 0.23 |
| 65 | 0.21 |
| 66 | 10.56 |
| 67 | 3.41 |
| 68 | 12.83 |
| 69 | 7.20 |
| 70 | 4.05 |
| 77 | 5.65 |
| 78 | 2.26 |
| 79 | 1.41 |
| 82 | 2.81 |
| 85 | 2.02 |
| 88 | 2.21 |
| 94 | 1.63 |
| 100 | 2.98 |
| 111 | 3.25 |
| 115 | 0.57 |
| 117 | 0.59 |
| 118 | 9.25 |
| 119 | 4.16 |
| 121 | 2.6 |
| 122 | 0.36 |
| 128 | 0.38 |
| 132 | 3.60 |
| 133 | 4.99 |
| 134 | 3.00 |
| 136 | 2.06 |
| 141 | 2.24 |
| 142 | 1.48 |
| 143 | 12.31 |
| 145 | 1.84 |
| 151 | 1.40 |
| 153 | 1.36 |
| 157 | 0.58 |
| 163 | 1.5 |
| 164 | 0.17 |
| 169 | 7.14 |
| 171 | 0.61 |
| 173 | 2.35 |
| 178 | 0.71 |
| 182 | 13.56 |
| 184 | 3.66 |
| 190 | 1.09 |
| 191 | 1.20 |
| 192 | 3.99 |
| 194 | 4.20 |

EXAMPLE 9

Cell Cytotoxicity Assay (1) Culturing of Cancer Cells

A549, HT29 and MCF-7 were used to measure anticancer activity. The cancer cells were those distributed from the National Cancer Institute (NCI) of the U.S. and cultured by the Korea Research Institute of Chemical Technology (KRICT), which had been derived from human tumor cell lines. The cells were cultured in a 5% $CO_2$ incubator at 37° C. with constant temperature and humidity using RPMI 1640 culture medium fortified with 5% fetal bovine serum. Sub-culturing was carried out once in 3-4 days. A PBS (phosphate buffered saline) solution in which 0.25% trypsin and 3 mm trans-1,2-diaminocyclohexane-N,N,N,N-tetraacetic acid (CDTA) were dissolved was used to separate the cells.

(2) Activity Measurement

The SRB (sulforhodamine B) assay method, which was developed in 1989 to measure in vitro anticancer activity of drugs by the NCI, was used. The cells were separated using a trypsin-CDTA solution and were plated on a 96-well microplate (Falcon), about $2 \times 10^3$ cells per each well. The cells were cultured in a $CO_2$ incubator for 24 hours and were attached to the bottom of the plate. After removing the culture medium using an aspirator, each of Compound No. 78, Compound No. 79 and Doxorubicin, a control drug, diluted in a culture medium was added to the wells containing the cells, with a log dose of 6 equivalents, 3 times, 100 mL at one time. The cells were cultured for 48 more hours. If required, dimethylsulfoxide (DMSO) was used to dissolve the compounds. The diluted compound solutions were filtered through a 0.22 mL filter before being added to the cells. After 48 hours of culturing, the culture medium was removed from each well and 100 mL of 10% trichloroacetic acid (TCA) was added. The cells were fixed to the plate by keeping the plate at 4° C. for 1 hour. Then, the plate was washed 5-6 times with water, in order to completely remove any remaining TCA, and dried at room temperature. To the dry plate was added a staining solution, in which 0.4% SRB was dissolved in 100 mL of 1% acetic acid solution per each well. After 30 minutes of staining, the plate was washed 5-6 times with 1% acetic acid solution to remove the SRB not bound to the cells. The stained cell plate was dried at room temperature. Then, 100 mL of 10 mm unbuffered trisma base solution was added, per each well, and the plate was shaken for 10 minutes with a titer plate shaker to elute the dye. Then, absorbance was measured at 520 nm using a microplate reader. In order to quantify the anticancer effect of the compounds, number of cells was counted for the cases where the drug was added ($T_z$), the cells were cultured for 48 hours with a culture medium containing no drug (C) and the cells were cultured for 48 hours with a culture medium containing the drug (T). Anticancer activity was calculated by the following equations 1 and 2.

$$\text{Antitumor activity} = \frac{T - T_z}{C - T_z} \times 100 \text{ (if } T_z > T\text{)} \quad \text{Equation 1}$$

$$\text{Antitumor activity} = \frac{T - T_z}{T_z} \times 100 \text{ (if } T_z < T\text{)} \quad \text{Equation 2}$$

The inhibitory effect of the drugs against growth of the cancer cells were obtained by data regression using the Lotus software in % of inhibition. The result is given in Table 3 below.

TABLE 3

| Cancer cell lines | A549 | HT29 | MCF-7 |
|---|---|---|---|
| Concentration | 10 μM (%) | 10 μM (%) | 10 μM (%) |
| Compound 78 | 67.5 | 59.7 | 67.3 |
| Compound 79 | 39.1 | 82.4 | 31.1 |
| Doxorubicin | 39 | 51.1 | 63.2 |

As seen in Table 3, the 5-(1,3-diaryl-1H-pyrazol-4-ylmethylene)-thiazolidine-2,4-dione derivatives represented by the formula 1 showed cytotoxicity to several cancer cells, including A-549 (non-small cell lung cancer), HT29 (liver cancer) and MCF-7 (breast cancer).

EXAMPLE 10

Comparison of In Vivo Anticancer Effect of Several Candidate CDC25B Inhibitors Using Human Tumor Model In order to verify the in vivo anticancer effect of the compounds of the present invention, C33A human uterine cancer cell line was subcutaneously injected at the abdominal walls of 6- to 8-week-old male nude mice. When the tumor grew to the size of about 50-80 mm$^3$, Compound No. 78 and 0.2% Tween 80, a negative control, were administered into the abdominal cavity, respectively. For a positive control, cisplatin (4 mg/kg), which is widely used as an anticancer agent in clinical tests, was used. The dosage given was 0.25 mL per each administration once a day for a period of 7 consecutive days. The volume of the tumor was calculated by the following equation 3, by measuring the long and short axes with a caliper.

$$\text{Tumor volume} = (\text{Short axis,mm})^2 \times (\text{Long axis,mm}) \times 0.523 \qquad \text{Equation 3}$$

The result is shown in FIG. 1. As seen in the FIGURE, Compound 78 showed an anticancer activity comparable to that of cisplatin, but it did not shows any negative responses, such as reduced motion or lack of appetite, which are caused by the toxicity of cisplatin. Thus, the 5-(1,3-diaryl-1H-pyrazol-4-ylmethylene)-thiazolidine-2,4-dione derivatives represented by the formula 1 can be utilized as low-toxicity anticancer agent with less side effects.

INDUSTRIAL APPLICABILITY

As apparent from the above description, the 5-(1,3-diaryl-1H-pyrazol-4-yl-methylene)-thiazolidine-2,4-dione derivatives represented by the formula 1 and its pharmaceutically acceptable salts thereof show superior inhibitory activities against CDC25B, which is a phosphatase playing an important role in determining G2/M phase transition during cell division. Further, due to less side effects, for example, reduced motion or lack of appetite, they can be used as a low-toxic anticancer agent.

While the present invention has been described in detail with reference to the preferred embodiments, those skilled in the art will appreciate that various modifications and substitutions can be made thereto without departing from the spirit and scope of the present invention as set forth in the appended claims.

The invention claimed is:

1. A compound represented by the following formula 1 or its pharmaceutically acceptable salt thereof:

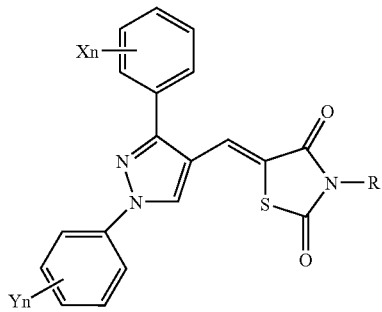

(1)

wherein
X is hydrogen, $C_1$-$C_4$alkyl, $C_1$-$C_4$haloalkyl, a halogen atom, $C_1$-$C_4$alkoxy, unsubstituted or substituted with $C_1$-$C_4$alkylcarboxyl, $C_1$-$C_4$haloalkoxy, $C_3$-$C_4$alkenyloxy, $C_2$-$C_4$acyl, $C_3$-$C_{10}$cycloalkylalkoxy, $C_3$-$C_{10}$cycloalkyloxy, hydroxy, cyano or nitro;

Y is hydrogen, $C_1$-$C_4$alkyl, a halogen atom, $C_1$-$C_4$alkoxy, $C_3$-$C_4$ alkenyloxy, $C_2$-$C_4$acyl, cyano or nitro;

n is an integer of from 1 to 5; and

R is hydrogen, $C_1$-$C_4$alkyl, $C_2$-$C_4$alkenyl, $C_3$-$C_4$alkynyl, $C_1$-$C_4$haloalkyl, $C_2$-$C_4$alkoxyalkyl or benzyl.

2. The compound represented by the formula 1 or the pharmaceutically acceptable salt thereof according to claim 1, wherein X is $C_1$-$C_4$alkyl, $C_1$-$C_4$haloalkyl, a halogen atom, $C_1$-$C_4$alkoxy un-substituted or substituted with $C_1$-$C_4$alkylcarboxyl, $C_1$-$C_4$haloalkoxy, $C_3$-$C_{10}$cycloalkylalkoxy, $C_3$-$C_{10}$cycloalkyloxy, hydroxy, $C_3$-$C_4$alkenyloxy or nitro;

Y is hydrogen, $C_1$-$C_4$alkyl, a halogen atom, $C_1$-$C_4$alkoxy, $C_3$-$C_4$alkenyloxy, $C_2$-$C_4$acyl, cyano or nitro;

n is an integer of from 1 to 3; and

R is hydrogen, $C_1$-$C_4$alkyl, $C_1$-$C_4$haloalkyl, $C_2$-$C_4$alkoxyalkyl or benzyl.

3. A method of preparing a compound represented by the formula 1 below or its pharmaceutically acceptable salt comprising:

reacting the compound represented by the formula 2 with the compound represented by the formula 3 to obtain the compound represented by the formula 4;

transforming the compound represented by the formula 4 to the compound represented by the formula 5 below by Vilsmeier-Haack reaction; and reacting the compound represented by the formula 5 with thiazolo-2,4-dione to obtain the compound represented by the formula 1, in which R is H, or reacting the product with the compound represented by the formula 6 to obtain the compound represented by the formula 1:

(1)

(2)

(3)

-continued
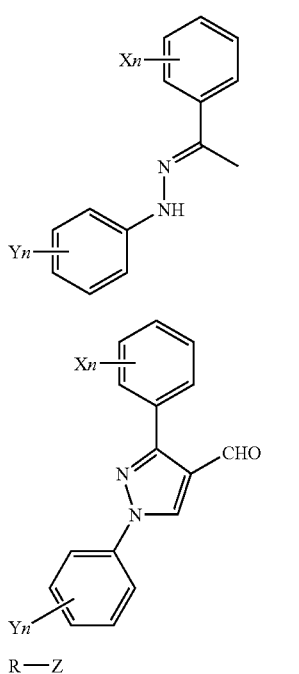
(4)
(5)
(6)
wherein
X, Y, n and R are the same as defined in claim 1; and
Z is a leaving group.
4. A composition comprising the compound represented by the following formula 1 or its pharmaceutically acceptable salts in a pharmaceutically effective amount:
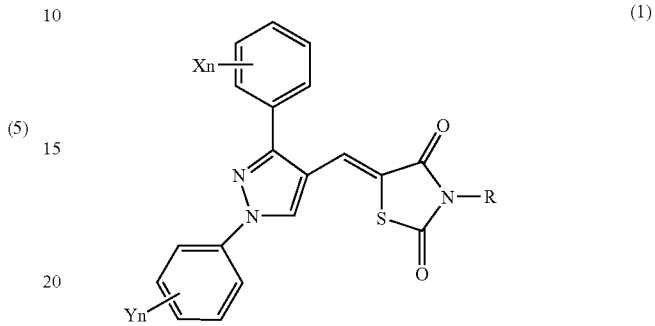
(1)
wherein
X, Y, n and R are the same as defined in claim 1.
* * * * *